(12) United States Patent
Chandler et al.

(10) Patent No.: US 9,694,163 B2
(45) Date of Patent: Jul. 4, 2017

(54) SURGICAL DEVICE FOR PERFORMING A SPHENOPALATINE GANGLION BLOCK PROCEDURE

(71) Applicant: BIOVISION TECHNOLOGIES, LLC, Golden, CO (US)

(72) Inventors: Stephen W. Chandler, Montgomery, AL (US); David W. Sanso, Morrison, CO (US)

(73) Assignee: Biovision Technologies, LLC, Golden, CO (US)

( * ) Notice: Subject to any disclaimer, the term of this patent is extended or adjusted under 35 U.S.C. 154(b) by 41 days.

(21) Appl. No.: 14/298,521

(22) Filed: Jun. 6, 2014

(65) Prior Publication Data
US 2015/0352341 A1    Dec. 10, 2015

Related U.S. Application Data

(60) Provisional application No. 61/917,097, filed on Dec. 17, 2013.

(51) Int. Cl.
| | |
|---|---|
| A61B 1/06 | (2006.01) |
| A61M 25/10 | (2013.01) |
| A61B 1/00 | (2006.01) |
| A61B 1/233 | (2006.01) |
| A61B 1/015 | (2006.01) |

(Continued)

(52) U.S. Cl.
CPC ... *A61M 25/10182* (2013.11); *A61B 1/00032* (2013.01); *A61B 1/00124* (2013.01); *A61B 1/015* (2013.01); *A61B 1/06* (2013.01); *A61B 1/233* (2013.01); *A61B 17/24* (2013.01); *A61B 2017/22067* (2013.01); *A61M 2025/1052* (2013.01); *A61M 2202/048* (2013.01); *A61M 2210/06* (2013.01)

(58) Field of Classification Search
CPC . A61M 27/00; A61M 31/00; A61M 25/10182
USPC ............... 600/249; 604/102.02, 506–509
See application file for complete search history.

(56) References Cited

U.S. PATENT DOCUMENTS

| | | | |
|---|---|---|---|
| 2,493,326 A | 1/1950 | Trinder | |
| 2,847,997 A | 8/1958 | Tibone | |
| 2,936,760 A | 5/1960 | Gants | |

(Continued)

FOREIGN PATENT DOCUMENTS

| CA | 2266958 A1 | 10/1999 |
|---|---|---|
| EP | 2522386 A2 | 11/2012 |

(Continued)

OTHER PUBLICATIONS

Agro, et al., "Lightwand intubation using the Trachlight(TM): a brief review of current knowledge," Canadian Journal of Anesthesia, (2000), pp. 592-599.

(Continued)

*Primary Examiner* — Ellen C Hammond
*Assistant Examiner* — Christina Negrellirodrigue
(74) *Attorney, Agent, or Firm* — Faegre Baker Daniels LLP

(57) ABSTRACT

Methods and devices quickly and accurately locate the sphenopalatine ganglion (SPG) while performing a sphenopalatine ganglion block procedure that introduces a medication to the SPG. The methods and devices also prevent the medication applied to the SPG from flowing down a patient's throat during the procedure.

14 Claims, 17 Drawing Sheets

(51) Int. Cl.
*A61B 17/24* (2006.01)
*A61B 17/22* (2006.01)

(56) References Cited

U.S. PATENT DOCUMENTS

| | | | |
|---|---|---|---|
| 3,049,125 A | 8/1962 | Kriwkowitsch |
| 3,664,330 A | 5/1972 | Deutsch |
| 3,747,595 A | 7/1973 | Grossan |
| 3,766,924 A | 10/1973 | Pidgeon |
| 3,800,788 A | 4/1974 | White |
| 3,850,176 A | 11/1974 | Gottschalk |
| 3,903,893 A | 9/1975 | Scheer |
| 4,592,357 A | 6/1986 | Ersek |
| 4,606,346 A | 8/1986 | Berg et al. |
| 4,819,619 A | 4/1989 | Augustine et al. |
| 4,883,465 A | 11/1989 | Brennan |
| 4,886,493 A | 12/1989 | Yee |
| 4,887,593 A | 12/1989 | Wiley et al. |
| 5,024,658 A | 6/1991 | Kozlov et al. |
| 5,116,311 A | 5/1992 | Lofstedt |
| 5,189,727 A | 2/1993 | Guerreri |
| 5,193,525 A | 3/1993 | Silverstein et al. |
| 5,213,115 A | 5/1993 | Zytkovicz et al. |
| 5,215,536 A | 6/1993 | Lampropoulos et al. |
| 5,242,400 A | 9/1993 | Blake et al. |
| 5,370,640 A | 12/1994 | Kolff |
| 5,446,070 A | 8/1995 | Mantelle |
| 5,462,553 A | 10/1995 | Dolgin |
| 5,483,951 A | 1/1996 | Frassica et al. |
| 5,514,128 A | 5/1996 | Hillsman et al. |
| 5,531,676 A | 7/1996 | Edwards et al. |
| 5,534,242 A | 7/1996 | Henry |
| 5,546,964 A | 8/1996 | Stangerup |
| 5,599,304 A | 2/1997 | Shaari |
| 5,626,553 A | 5/1997 | Frassica et al. |
| 5,647,847 A | 7/1997 | Lafontaine et al. |
| 5,667,476 A | 9/1997 | Frassica et al. |
| 5,676,635 A | 10/1997 | Levin |
| 5,685,822 A | 11/1997 | Harhen |
| 5,718,666 A | 2/1998 | Alarcon |
| 5,735,817 A | 4/1998 | Shantha |
| 5,752,971 A | 5/1998 | Rosenbluth et al. |
| 5,792,100 A | 8/1998 | Shantha |
| 5,819,727 A | 10/1998 | Linder |
| 5,827,177 A | 10/1998 | Oneda et al. |
| 5,827,224 A | 10/1998 | Shippert |
| 5,858,331 A | 1/1999 | Henry |
| 5,876,329 A | 3/1999 | Harhen |
| 6,027,478 A | 2/2000 | Katz |
| 6,106,496 A | 8/2000 | Arnissolle |
| 6,174,280 B1 | 1/2001 | Oneda et al. |
| 6,190,330 B1 | 2/2001 | Harhen |
| 6,258,101 B1 | 7/2001 | Blake et al. |
| 6,322,542 B1 | 11/2001 | Nilson et al. |
| 6,350,231 B1 | 2/2002 | Ailinger et al. |
| 6,350,465 B1 | 2/2002 | Jonnalagadda et al. |
| 6,394,093 B1 | 5/2002 | Lethi |
| 6,413,499 B1 | 7/2002 | Clay |
| 6,432,986 B2 | 8/2002 | Levin |
| 6,461,294 B1 | 10/2002 | Oneda et al. |
| 6,491,940 B1 | 12/2002 | Levin |
| 6,529,756 B1 | 3/2003 | Phan et al. |
| 6,530,881 B1 | 3/2003 | Ailinger et al. |
| 6,579,582 B1 | 6/2003 | Harhen et al. |
| D478,987 S | 8/2003 | Groenke et al. |
| 6,607,546 B1 | 8/2003 | Murken |
| 6,669,711 B1 | 12/2003 | Noda |
| 6,677,321 B1 | 1/2004 | Levin |
| 6,693,670 B1 | 2/2004 | Stark |
| 6,733,440 B2 | 5/2004 | Ailinger et al. |
| 6,740,030 B2 | 5/2004 | Martone et al. |
| 6,758,840 B2 | 7/2004 | Knox |
| 6,770,080 B2 | 8/2004 | Kaplan et al. |
| 6,793,661 B2 | 9/2004 | Hamilton et al. |
| 6,822,213 B2 | 11/2004 | Stark |
| 6,853,858 B2 | 2/2005 | Shalev |
| 6,902,535 B2 | 6/2005 | Eberhart et al. |
| 7,025,923 B2 | 4/2006 | Harhen et al. |
| 7,056,284 B2 | 6/2006 | Martone et al. |
| 7,056,287 B2 | 6/2006 | Taylor et al. |
| 7,081,097 B2 | 7/2006 | Martone et al. |
| 7,112,578 B2 | 9/2006 | Levin |
| 7,117,033 B2 | 10/2006 | Shalev et al. |
| 7,120,489 B2 | 10/2006 | Shalev et al. |
| 7,131,969 B1 | 11/2006 | Hovda et al. |
| D534,216 S | 12/2006 | Makower et al. |
| 7,146,209 B2 | 12/2006 | Gross et al. |
| 7,169,161 B2 | 1/2007 | Bonnette et al. |
| 7,190,998 B2 | 3/2007 | Shalev et al. |
| D544,602 S | 6/2007 | Hughett et al. |
| 7,336,309 B2 | 2/2008 | Stark |
| 7,361,168 B2 | 4/2008 | Makower et al. |
| 7,410,480 B2 | 8/2008 | Muni et al. |
| 7,419,497 B2 | 9/2008 | Muni et al. |
| 7,462,175 B2 | 12/2008 | Chang et al. |
| 7,500,971 B2 | 3/2009 | Chang et al. |
| 7,507,200 B2 | 3/2009 | Okada |
| 7,520,876 B2 | 4/2009 | Ressemann et al. |
| 7,559,925 B2 | 7/2009 | Goldfarb et al. |
| 7,561,919 B2 | 7/2009 | Shalev et al. |
| 7,636,597 B2 | 12/2009 | Gross et al. |
| 7,640,062 B2 | 12/2009 | Shalev |
| 7,641,644 B2 | 1/2010 | Chang et al. |
| 7,642,563 B2 | 1/2010 | Kang et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,678,099 B2 | 3/2010 | Ressemann et al. |
| 7,684,859 B2 | 3/2010 | Shalev et al. |
| 7,704,259 B2 | 4/2010 | Kaplan et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,729,759 B2 | 6/2010 | Shalev et al. |
| 7,740,642 B2 | 6/2010 | Becker |
| 7,749,515 B2 | 7/2010 | Blumenfeld |
| 7,753,929 B2 | 7/2010 | Becker |
| 7,753,930 B2 | 7/2010 | Becker |
| 7,771,409 B2 | 8/2010 | Chang et al. |
| 7,785,315 B1 | 8/2010 | Muni et al. |
| 7,799,337 B2 | 9/2010 | Levin |
| 7,803,150 B2 | 9/2010 | Chang et al. |
| 7,837,672 B2 | 11/2010 | Intoccia |
| 7,842,062 B2 | 11/2010 | Keith et al. |
| 7,854,744 B2 | 12/2010 | Becker |
| 7,877,147 B2 | 1/2011 | Shalev et al. |
| 7,879,011 B2 | 2/2011 | Chang |
| 7,879,061 B2 | 2/2011 | Keith et al. |
| 7,908,000 B2 | 3/2011 | Shalev |
| 7,918,871 B2 | 4/2011 | Truitt et al. |
| D640,374 S | 6/2011 | Liu et al. |
| D643,115 S | 8/2011 | Gonzales et al. |
| 8,010,189 B2 | 8/2011 | Shalev |
| 8,012,084 B2 | 9/2011 | Machida |
| 8,025,635 B2 | 9/2011 | Eaton et al. |
| 8,052,693 B2 | 11/2011 | Shahoian |
| 8,080,000 B2 | 12/2011 | Makower et al. |
| 8,088,101 B2 | 1/2012 | Chang et al. |
| 8,090,433 B2 | 1/2012 | Makower et al. |
| 8,100,933 B2 | 1/2012 | Becker |
| 8,114,062 B2 | 2/2012 | Muni et al. |
| 8,114,113 B2 | 2/2012 | Becker |
| 8,118,757 B2 | 2/2012 | Morriss |
| 8,123,722 B2 | 2/2012 | Chang et al. |
| 8,142,422 B2 | 3/2012 | Makower et al. |
| D658,291 S | 4/2012 | Jenkins et al. |
| 8,146,400 B2 | 4/2012 | Goldfarb et al. |
| 8,172,828 B2 | 5/2012 | Chang et al. |
| 8,182,432 B2 | 5/2012 | Kim et al. |
| 8,190,389 B2 | 5/2012 | Kim et al. |
| 8,192,420 B2 | 6/2012 | Morriss et al. |
| 8,224,438 B2 | 7/2012 | Levin |
| 8,229,571 B2 | 7/2012 | Lorian et al. |

(56) References Cited

U.S. PATENT DOCUMENTS

| | | |
|---|---|---|
| 8,231,588 B2 | 7/2012 | Xia |
| 8,241,266 B2 | 8/2012 | Keith et al. |
| 8,241,641 B2 | 8/2012 | Blumenfeld |
| 8,249,700 B2 | 8/2012 | Clifford et al. |
| 8,277,478 B2 | 10/2012 | Drontle et al. |
| 8,282,667 B2 | 10/2012 | Drontle et al. |
| 8,308,709 B2 | 11/2012 | Chang |
| 8,313,520 B2 | 11/2012 | Barbut et al. |
| 8,317,816 B2 | 11/2012 | Becker |
| 8,337,454 B2 | 12/2012 | Eaton et al. |
| 8,348,969 B2 | 1/2013 | Keith et al. |
| 8,360,968 B2 | 1/2013 | Hadani |
| 8,388,600 B1 | 3/2013 | Eldredge |
| 8,388,642 B2 | 3/2013 | Muni et al. |
| 8,412,336 B2 | 4/2013 | Pless et al. |
| 8,414,473 B2 | 4/2013 | Jenkins et al. |
| 8,425,457 B2 | 4/2013 | John et al. |
| 8,425,488 B2 | 4/2013 | Clifford et al. |
| 8,435,290 B2 | 5/2013 | Clifford et al. |
| 8,439,687 B1 | 5/2013 | Morriss et al. |
| 8,452,392 B2 | 5/2013 | Morriss et al. |
| D683,852 S | 6/2013 | Gonzales et al. |
| 8,480,658 B1 | 7/2013 | Nakao |
| 8,485,199 B2 | 7/2013 | Morriss |
| 8,486,155 B2 | 7/2013 | McAlister et al. |
| 8,568,439 B2 | 10/2013 | Keith et al. |
| 8,585,728 B2 | 11/2013 | Keith et al. |
| 8,585,729 B2 | 11/2013 | Keith et al. |
| 8,623,043 B1 | 1/2014 | Keith et al. |
| 8,636,684 B2 | 1/2014 | Deem et al. |
| 8,657,846 B2 | 2/2014 | Keith et al. |
| 8,690,839 B2 | 4/2014 | Xia et al. |
| 8,702,626 B1 | 4/2014 | Kim et al. |
| 8,715,169 B2 | 5/2014 | Chang et al. |
| 8,721,591 B2 | 5/2014 | Chang et al. |
| 8,740,839 B2 | 6/2014 | Eaton et al. |
| 8,740,929 B2 | 6/2014 | Gopferich et al. |
| 8,747,389 B2 | 6/2014 | Goldfarb et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,764,786 B2 | 7/2014 | Becker |
| 8,777,926 B2 | 7/2014 | Chang et al. |
| 8,801,670 B2 | 8/2014 | Drontle et al. |
| 8,828,041 B2 | 9/2014 | Chang et al. |
| 8,834,513 B2 | 9/2014 | Hanson et al. |
| 8,852,143 B2 | 10/2014 | Chang et al. |
| 8,858,551 B2 | 10/2014 | Naito |
| 8,858,586 B2 | 10/2014 | Chang et al. |
| 8,858,974 B2 | 10/2014 | Eaton et al. |
| 8,864,787 B2 | 10/2014 | Muni et al. |
| 8,876,794 B2 | 11/2014 | Xia |
| 8,882,795 B2 | 11/2014 | Drontle et al. |
| 8,888,686 B2 | 11/2014 | Drontle et al. |
| 8,894,614 B2 | 11/2014 | Muni et al. |
| 8,905,922 B2 | 12/2014 | Makower et al. |
| 8,905,980 B2 | 12/2014 | Xia |
| 8,915,938 B2 | 12/2014 | Keith et al. |
| 8,932,276 B1 | 1/2015 | Morriss et al. |
| 8,954,149 B2 | 2/2015 | Shalev |
| 8,956,280 B2 | 2/2015 | Eversull et al. |
| 8,961,398 B2 | 2/2015 | Makower et al. |
| 8,986,340 B2 | 3/2015 | Drontle et al. |
| D730,515 S | 5/2015 | Shahidi Bonjar |
| D735,848 S | 8/2015 | Dubuc et al. |
| D736,922 S | 8/2015 | Allen et al. |
| 2001/0002999 A1 | 6/2001 | Neuser et al. |
| 2001/0004644 A1 | 6/2001 | Levin |
| 2002/0010194 A1 | 1/2002 | Levin |
| 2002/0062119 A1 | 5/2002 | Zadno-Azizi |
| 2002/0161379 A1 | 10/2002 | Kaplan et al. |
| 2003/0120256 A1* | 6/2003 | Lary ............... A61M 25/00 604/509 |
| 2003/0133877 A1 | 7/2003 | Levin |
| 2003/0208249 A1 | 11/2003 | Chen |
| 2004/0064150 A1 | 4/2004 | Becker |
| 2004/0116958 A1 | 6/2004 | Gopferich et al. |
| 2004/0243172 A1 | 12/2004 | Hogle |
| 2005/0072430 A1 | 4/2005 | Djupesland |
| 2005/0080357 A1 | 4/2005 | Eberhart et al. |
| 2005/0113798 A1 | 5/2005 | Slater et al. |
| 2005/0124856 A1 | 6/2005 | Fujikura et al. |
| 2005/0228452 A1 | 10/2005 | Mourlas et al. |
| 2005/0240147 A1 | 10/2005 | Makower et al. |
| 2005/0245894 A1 | 11/2005 | Zadno-Azizi |
| 2005/0245906 A1 | 11/2005 | Makower et al. |
| 2005/0281751 A1 | 12/2005 | Levin |
| 2006/0004286 A1 | 1/2006 | Chang et al. |
| 2006/0004323 A1 | 1/2006 | Chang et al. |
| 2006/0063973 A1 | 3/2006 | Makower et al. |
| 2006/0095066 A1 | 5/2006 | Chang et al. |
| 2006/0106361 A1 | 5/2006 | Muni et al. |
| 2006/0155304 A1 | 7/2006 | Kaplan et al. |
| 2006/0161044 A1 | 7/2006 | Oneda et al. |
| 2006/0167439 A1 | 7/2006 | Kalser et al. |
| 2006/0189844 A1 | 8/2006 | Tien |
| 2006/0189847 A1 | 8/2006 | Yee et al. |
| 2006/0210605 A1 | 9/2006 | Chang et al. |
| 2007/0015964 A1 | 1/2007 | Eversull et al. |
| 2007/0020254 A1 | 1/2007 | Levin |
| 2007/0043327 A1 | 2/2007 | Knox |
| 2007/0073269 A1 | 3/2007 | Becker |
| 2007/0112257 A1 | 5/2007 | Hensler |
| 2007/0119451 A1 | 5/2007 | Wang et al. |
| 2007/0129705 A1 | 6/2007 | Trombley et al. |
| 2007/0129751 A1 | 6/2007 | Muni et al. |
| 2007/0135789 A1 | 6/2007 | Chang et al. |
| 2007/0142709 A1 | 6/2007 | Martone et al. |
| 2007/0167682 A1 | 7/2007 | Goldfarb et al. |
| 2007/0179518 A1 | 8/2007 | Becker |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0250105 A1 | 10/2007 | Ressemann et al. |
| 2007/0260264 A1 | 11/2007 | Nobis et al. |
| 2007/0265618 A1 | 11/2007 | Long |
| 2007/0267011 A1 | 11/2007 | Deem et al. |
| 2007/0282305 A1 | 12/2007 | Goldfarb et al. |
| 2007/0293726 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0004613 A1 | 1/2008 | Barbut et al. |
| 2008/0015472 A1 | 1/2008 | Ressemann et al. |
| 2008/0015540 A1 | 1/2008 | Muni et al. |
| 2008/0082045 A1 | 4/2008 | Goldfarb et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0125720 A1 | 5/2008 | Kim et al. |
| 2008/0132938 A1 | 6/2008 | Chang et al. |
| 2008/0154237 A1 | 6/2008 | Chang et al. |
| 2008/0154250 A1 | 6/2008 | Makower et al. |
| 2008/0172033 A1 | 7/2008 | Keith et al. |
| 2008/0183128 A1 | 7/2008 | Morriss et al. |
| 2008/0195041 A1 | 8/2008 | Goldfarb et al. |
| 2008/0208242 A1 | 8/2008 | Becker |
| 2008/0208243 A1 | 8/2008 | Becker |
| 2008/0215082 A1 | 9/2008 | Becker |
| 2008/0215083 A1 | 9/2008 | Becker |
| 2008/0228085 A1 | 9/2008 | Jenkins et al. |
| 2008/0234720 A1 | 9/2008 | Chang et al. |
| 2008/0243140 A1 | 10/2008 | Gopferich et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |

(56) References Cited

U.S. PATENT DOCUMENTS

| | | |
|---|---|---|
| 2008/0262510 A1 | 10/2008 | Clifford |
| 2008/0269643 A1 | 10/2008 | Morriss |
| 2008/0275483 A1 | 11/2008 | Makower et al. |
| 2008/0279895 A1 | 11/2008 | Blumenfeld |
| 2008/0281156 A1 | 11/2008 | Makower et al. |
| 2008/0281300 A1 | 11/2008 | Morriss |
| 2008/0281349 A2 | 11/2008 | Becker |
| 2008/0287908 A1 | 11/2008 | Muni et al. |
| 2008/0293999 A1 | 11/2008 | Halahmi |
| 2008/0319424 A1 | 12/2008 | Muni et al. |
| 2009/0005763 A1 | 1/2009 | Makower et al. |
| 2009/0028923 A1 | 1/2009 | Muni et al. |
| 2009/0030274 A1 | 1/2009 | Goldfarb et al. |
| 2009/0054803 A1 | 2/2009 | Saadat et al. |
| 2009/0076331 A1 | 3/2009 | Konwitz et al. |
| 2009/0093823 A1 | 4/2009 | Chang et al. |
| 2009/0125046 A1 | 5/2009 | Becker |
| 2009/0156980 A1 | 6/2009 | Eaton et al. |
| 2009/0163848 A1 | 6/2009 | Morriss et al. |
| 2009/0163890 A1 | 6/2009 | Clifford et al. |
| 2009/0171301 A1 | 7/2009 | Becker |
| 2009/0181074 A1 | 7/2009 | Makower et al. |
| 2009/0187098 A1 | 7/2009 | Makower et al. |
| 2009/0198216 A1 | 8/2009 | Muni et al. |
| 2009/0214466 A1 | 8/2009 | Levin |
| 2009/0227900 A1 | 9/2009 | Kim et al. |
| 2009/0240112 A1 | 9/2009 | Goldfarb et al. |
| 2009/0240237 A1 | 9/2009 | Goldfarb et al. |
| 2009/0306588 A1 | 12/2009 | Nguyen et al. |
| 2009/0312696 A1 | 12/2009 | Copa et al. |
| 2009/0312745 A1 | 12/2009 | Goldfarb et al. |
| 2009/0318797 A1 | 12/2009 | Hadani |
| 2010/0010302 A1 | 1/2010 | Hadani |
| 2010/0016844 A1 | 1/2010 | Patel et al. |
| 2010/0030031 A1 | 2/2010 | Goldfarb et al. |
| 2010/0030113 A1 | 2/2010 | Morriss et al. |
| 2010/0030131 A1 | 2/2010 | Morriss et al. |
| 2010/0030187 A1 | 2/2010 | Xia |
| 2010/0030188 A1 | 2/2010 | Xia |
| 2010/0042046 A1 | 2/2010 | Chang et al. |
| 2010/0056867 A1 | 3/2010 | LaBombard et al. |
| 2010/0057048 A1 | 3/2010 | Eldredge |
| 2010/0076269 A1 | 3/2010 | Makower et al. |
| 2010/0081873 A1 | 4/2010 | Tanimura et al. |
| 2010/0099946 A1 | 4/2010 | Jenkins et al. |
| 2010/0100181 A1 | 4/2010 | Makower et al. |
| 2010/0105983 A1 | 4/2010 | Oneda et al. |
| 2010/0114066 A1 | 5/2010 | Makower et al. |
| 2010/0114184 A1 | 5/2010 | Degtyar et al. |
| 2010/0121308 A1 | 5/2010 | Muni et al. |
| 2010/0152730 A1 | 6/2010 | Makower et al. |
| 2010/0168511 A1 | 7/2010 | Muni et al. |
| 2010/0174138 A1 | 7/2010 | Chang et al. |
| 2010/0174196 A1 | 7/2010 | Ryan et al. |
| 2010/0174308 A1 | 7/2010 | Chang et al. |
| 2010/0179488 A1 | 7/2010 | Spiegel et al. |
| 2010/0179511 A1 | 7/2010 | Rajan et al. |
| 2010/0198135 A1 | 8/2010 | Morriss et al. |
| 2010/0198191 A1 | 8/2010 | Clifford et al. |
| 2010/0198247 A1 | 8/2010 | Chang et al. |
| 2010/0210901 A1 | 8/2010 | Makower et al. |
| 2010/0211005 A1 | 8/2010 | Edwards et al. |
| 2010/0211007 A1 | 8/2010 | Lesch et al. |
| 2010/0211140 A1 | 8/2010 | Barbut et al. |
| 2010/0217296 A1 | 8/2010 | Morriss et al. |
| 2010/0241068 A1 | 9/2010 | Chen |
| 2010/0241155 A1 | 9/2010 | Chang et al. |
| 2010/0256653 A1 | 10/2010 | Kaplan et al. |
| 2010/0268245 A1 | 10/2010 | Chang et al. |
| 2010/0274188 A1 | 10/2010 | Chang et al. |
| 2010/0274222 A1 | 10/2010 | Setliff et al. |
| 2010/0280626 A1 | 11/2010 | Shalon et al. |
| 2010/0282246 A1 | 11/2010 | Djupesland et al. |
| 2010/0286659 A1 | 11/2010 | Terrill et al. |
| 2010/0292765 A1 | 11/2010 | Etwil |
| 2010/0298640 A1 | 11/2010 | Oneda et al. |
| 2010/0298862 A1 | 11/2010 | Chang et al. |
| 2010/0305697 A1 | 12/2010 | Clifford et al. |
| 2010/0324483 A1 | 12/2010 | Rozenberg et al. |
| 2011/0004057 A1 | 1/2011 | Goldfarb et al. |
| 2011/0004058 A1 | 1/2011 | Oneda et al. |
| 2011/0004192 A1 | 1/2011 | Eaton et al. |
| 2011/0004194 A1 | 1/2011 | Eaton et al. |
| 2011/0015645 A1 | 1/2011 | Liu et al. |
| 2011/0015734 A1 | 1/2011 | Gonzales et al. |
| 2011/0020279 A1 | 1/2011 | Shantha |
| 2011/0054395 A1 | 3/2011 | O'Dea et al. |
| 2011/0060214 A1 | 3/2011 | Makower |
| 2011/0087192 A1 | 4/2011 | Uhland et al. |
| 2011/0098659 A1 | 4/2011 | Covello |
| 2011/0112512 A1 | 5/2011 | Muni et al. |
| 2011/0152838 A1 | 6/2011 | Xia |
| 2011/0160623 A1 | 6/2011 | Shalev |
| 2011/0160740 A1 | 6/2011 | Makower et al. |
| 2011/0208215 A1 | 8/2011 | Modesitt et al. |
| 2011/0224652 A1 | 9/2011 | Drontle et al. |
| 2011/0245765 A1 | 10/2011 | Jacobsen et al. |
| 2011/0288559 A1 | 11/2011 | Shahoian |
| 2011/0318345 A1 | 12/2011 | Djupesland |
| 2012/0010646 A1 | 1/2012 | Keith et al. |
| 2012/0017893 A1 | 1/2012 | Xia |
| 2012/0046607 A1 | 2/2012 | Syk |
| 2012/0053404 A1 | 3/2012 | Schreck et al. |
| 2012/0071715 A1 | 3/2012 | Beyar et al. |
| 2012/0071727 A1 | 3/2012 | Hanson et al. |
| 2012/0071824 A1 | 3/2012 | Chang et al. |
| 2012/0071856 A1 | 3/2012 | Goldfarb et al. |
| 2012/0071857 A1 | 3/2012 | Goldfarb et al. |
| 2012/0078118 A1 | 3/2012 | Jenkins et al. |
| 2012/0078377 A1* | 3/2012 | Gonzales ............... A61B 18/02 623/23.7 |
| 2012/0089028 A1 | 4/2012 | Hadani et al. |
| 2012/0090620 A1 | 4/2012 | Deutsch |
| 2012/0101343 A1 | 4/2012 | Duffy et al. |
| 2012/0116254 A1 | 5/2012 | Morriss |
| 2012/0128683 A1 | 5/2012 | Shantha |
| 2012/0136207 A1 | 5/2012 | Goldfarb et al. |
| 2012/0157968 A1 | 6/2012 | Eldredge et al. |
| 2012/0172751 A1 | 7/2012 | Levin |
| 2012/0172835 A1 | 7/2012 | Becker |
| 2012/0184983 A1 | 7/2012 | Chang et al. |
| 2012/0220923 A1 | 8/2012 | Morriss et al. |
| 2012/0221034 A1 | 8/2012 | Dinger et al. |
| 2012/0227457 A1 | 9/2012 | Kim et al. |
| 2012/0245419 A1 | 9/2012 | Makower et al. |
| 2012/0245456 A1 | 9/2012 | Kim et al. |
| 2012/0259215 A1 | 10/2012 | Gerrans et al. |
| 2012/0259216 A1 | 10/2012 | Gerrans et al. |
| 2012/0265094 A1 | 10/2012 | Goldfarb et al. |
| 2012/0277578 A1 | 11/2012 | Gunday et al. |
| 2012/0302825 A1 | 11/2012 | Schaeffer et al. |
| 2012/0310145 A1 | 12/2012 | Clifford et al. |
| 2012/0323214 A1 | 12/2012 | Shantha |
| 2013/0006055 A1 | 1/2013 | Goldfarb et al. |
| 2013/0018431 A1 | 1/2013 | Levin |
| 2013/0030458 A1 | 1/2013 | Drontle et al. |
| 2013/0041463 A1 | 2/2013 | Ressemann |
| 2013/0053644 A1 | 2/2013 | Smith et al. |
| 2013/0053824 A1 | 2/2013 | Seiden et al. |
| 2013/0066358 A1 | 3/2013 | Nalluri et al. |
| 2013/0072958 A1 | 3/2013 | Ressemann et al. |
| 2013/0073015 A1 | 3/2013 | Rozenberg |
| 2013/0085472 A1 | 4/2013 | Shaari |
| 2013/0090544 A1 | 4/2013 | Clifford et al. |
| 2013/0096605 A1 | 4/2013 | Becker |
| 2013/0103023 A1 | 4/2013 | Monson et al. |
| 2013/0123833 A1 | 5/2013 | Lesch et al. |
| 2013/0130145 A1 | 5/2013 | Kaeding et al. |
| 2013/0158475 A1 | 6/2013 | Xia et al. |
| 2013/0165873 A1 | 6/2013 | Morriss et al. |
| 2013/0172852 A1 | 7/2013 | Chang |
| 2013/0184532 A1 | 7/2013 | Goldfarb et al. |
| 2013/0184568 A1 | 7/2013 | Muni et al. |
| 2013/0184574 A1 | 7/2013 | Newhauser et al. |

(56) References Cited

U.S. PATENT DOCUMENTS

| | | |
|---|---|---|
| 2013/0184683 A1 | 7/2013 | Chow et al. |
| 2013/0190678 A1 | 7/2013 | Andreas et al. |
| 2013/0197426 A1 | 8/2013 | Morriss et al. |
| 2013/0231529 A1 | 9/2013 | John et al. |
| 2013/0245608 A1 | 9/2013 | Muni et al. |
| 2013/0245609 A1* | 9/2013 | Schaeffer ............... A61B 17/24 604/514 |
| 2013/0261388 A1 | 10/2013 | Jenkins et al. |
| 2013/0274600 A1 | 10/2013 | Jenkins et al. |
| 2013/0274651 A1 | 10/2013 | Barbut et al. |
| 2013/0274715 A1 | 10/2013 | Chan et al. |
| 2013/0276794 A1 | 10/2013 | Morriss |
| 2013/0281982 A1 | 10/2013 | Makower et al. |
| 2013/0302445 A1 | 11/2013 | Barbut et al. |
| 2013/0303968 A1 | 11/2013 | Clifford et al. |
| 2013/0324970 A1 | 12/2013 | Arcand et al. |
| 2013/0325052 A1 | 12/2013 | Chang et al. |
| 2014/0012182 A1 | 1/2014 | Shantha |
| 2014/0018775 A1 | 1/2014 | Swords et al. |
| 2014/0030520 A1 | 1/2014 | Nakamura et al. |
| 2014/0031726 A1 | 1/2014 | Chernomorsky et al. |
| 2014/0031792 A1 | 1/2014 | Darin et al. |
| 2014/0066901 A1 | 3/2014 | Dinger et al. |
| 2014/0066928 A1 | 3/2014 | Bennett et al. |
| 2014/0073858 A1 | 3/2014 | Sherwinter |
| 2014/0074065 A1 | 3/2014 | Muni et al. |
| 2014/0074140 A1 | 3/2014 | Johnson et al. |
| 2014/0074141 A1 | 3/2014 | Johnson et al. |
| 2014/0088498 A1 | 3/2014 | Stevens et al. |
| 2014/0094733 A1 | 4/2014 | Clopp et al. |
| 2014/0107404 A1 | 4/2014 | Gruber |
| 2014/0107427 A1 | 4/2014 | Chow et al. |
| 2014/0114233 A1 | 4/2014 | Deem et al. |
| 2014/0135587 A1 | 5/2014 | Hess |
| 2014/0163072 A1 | 6/2014 | Romon-de-Jesus |
| 2014/0180328 A1 | 6/2014 | Vaccaro et al. |
| 2014/0200443 A1 | 7/2014 | Chang et al. |
| 2014/0200444 A1 | 7/2014 | Kim et al. |
| 2014/0213968 A1 | 7/2014 | Vaccaro et al. |
| 2014/0218904 A1 | 8/2014 | Cayton |
| 2014/0238398 A1 | 8/2014 | Christopher et al. |
| 2014/0242064 A1 | 8/2014 | Morriss et al. |
| 2014/0243792 A1 | 8/2014 | Berman et al. |
| 2014/0243793 A1 | 8/2014 | Morriss et al. |
| 2014/0243876 A1 | 8/2014 | Suehara |
| 2014/0276624 A1 | 9/2014 | Jeppson |
| 2014/0276626 A1 | 9/2014 | Jenkins et al. |
| 2014/0276627 A1 | 9/2014 | Jenkins et al. |
| 2014/0277072 A1 | 9/2014 | Suehara |
| 2014/0288623 A1 | 9/2014 | Levin |
| 2014/0295728 A1 | 10/2014 | Cayton |
| 2014/0296898 A1 | 10/2014 | Chang et al. |
| 2014/0324093 A1 | 10/2014 | Chang et al. |
| 2014/0330074 A1 | 11/2014 | Morriss et al. |
| 2014/0336575 A1 | 11/2014 | Muni et al. |
| 2014/0336693 A1 | 11/2014 | Goldfarb et al. |
| 2014/0336694 A1 | 11/2014 | Becker |
| 2014/0350520 A1 | 11/2014 | Drontle et al. |
| 2015/0038901 A1 | 2/2015 | Lampropoulos et al. |
| 2015/0039014 A1 | 2/2015 | Schaeffer et al. |
| 2015/0045825 A1 | 2/2015 | Caplan et al. |
| 2015/0065872 A1 | 3/2015 | Drake et al. |
| 2015/0065995 A1 | 3/2015 | Sanchez et al. |
| 2015/0141819 A1 | 5/2015 | Linden et al. |
| 2015/0141915 A1 | 5/2015 | Lampropoulos et al. |
| 2015/0164309 A1 | 6/2015 | Chandler et al. |
| 2015/0174406 A1 | 6/2015 | Lamensdorf et al. |
| 2015/0230700 A1 | 8/2015 | Chandler |
| 2015/0258315 A1 | 9/2015 | Chandler et al. |

FOREIGN PATENT DOCUMENTS

| | | |
|---|---|---|
| EP | 2522586 A2 | 11/2012 |
| KR | 20050117277 A | 12/2005 |
| KR | 1020050117277 A | 4/2006 |
| KR | 1020120013930 A | 2/2012 |
| WO | 0205703 A1 | 1/2002 |
| WO | 0207632 A1 | 1/2002 |
| WO | 2006020180 A2 | 2/2006 |
| WO | 2010078145 A1 | 7/2010 |
| WO | 2015095214 A1 | 6/2015 |

OTHER PUBLICATIONS

Borris, et al., "Intraoperative nasal transillumination for maxillary sinus augmentation procedures: A technical note," International Journal of Oral and Maxillofacial Implants, vol. 13, Issue 4 (Jul.-Aug. 1998), pp. 569-570 (abstract only).

Cohen, et al., "Transnasal Illumination to Guide the Craniofacial Resection of Anterior Skull Base Neoplasms," Surgical Neurology, vol. 40 (1993), pp. 420-423.

Dolor, et al., "Management of Rhinosinusitis in Adults: Clinical Applications of Recent Evidence and Treatment Recommendations," Journal of Clinical Outcomes Management, vol. 9, No. 8 (Aug. 2002), pp. 463-476.

Felisati, "Headache & Migraine; Sphenopalatine endoscopic ganglion block alleviates cluster headache symptoms," Life Science Weekly (Oct. 10, 2006), pp. 741.

Friedman, et al., "Intraoperative and Postoperative Assessment of Frontal Sinus Patency by Transillumination," The Laryngoscope, vol. 110 (Apr. 2000), pp. 683-684.

Hung, et al., "Lightwand intubation: II—Clinical trial of a new lightwand for tracheal intubation in patients with difficult airways," Canadian Journal of Anaesthesia, vol. 42, Issue 9 (1995), pp. 826-830.

International Search Report and Written Opinion issued in PCT/US2014/070642, mailed Apr. 9, 2015, 16 pages.

International Search Report and Written Opinion issued in PCT/US2014/070905, mailed Apr. 24, 2015, 15 pages.

Massengill, "An Objective Technique for Submucous Cleft Palate Detection," Plastic and Reconstructive Surgery, vol. 37, No. 4 (1966), pp. 355-359.

Miyazaki, et al., "Fiberscopic Methods for Assessment of Velopharyngeal Closure during Various Activities," presented at the 15th annual convention of the Japan Society of Oral Surgery in Nagoya, Oct. 1970; presented at the 25th annual convention of the Japan Society of Oral Medicine in Tokyo, Apr. 1971; and presented at the 2nd International Cleft Palate Congress in Copenhagen, Aug. 1973.

Petroianu, et al., "Intubation with Transillumination: Nasal or Oral?," Prehospital and Disaster Medicine, vol. 14, No. 2 (Apr.-Jun. 1999), pp. 72-73.

WelchAllyn® 3.5v Transilluminators product brochure, date unknown.

WelchAllyn® PocketScopes™ Operating Instruction Manual, date unknown.

International Preliminary Report on Patentability issued in PCT/US2014/070642, mailed Jun. 30, 2016, 13 pages.

\* cited by examiner

DETAIL A

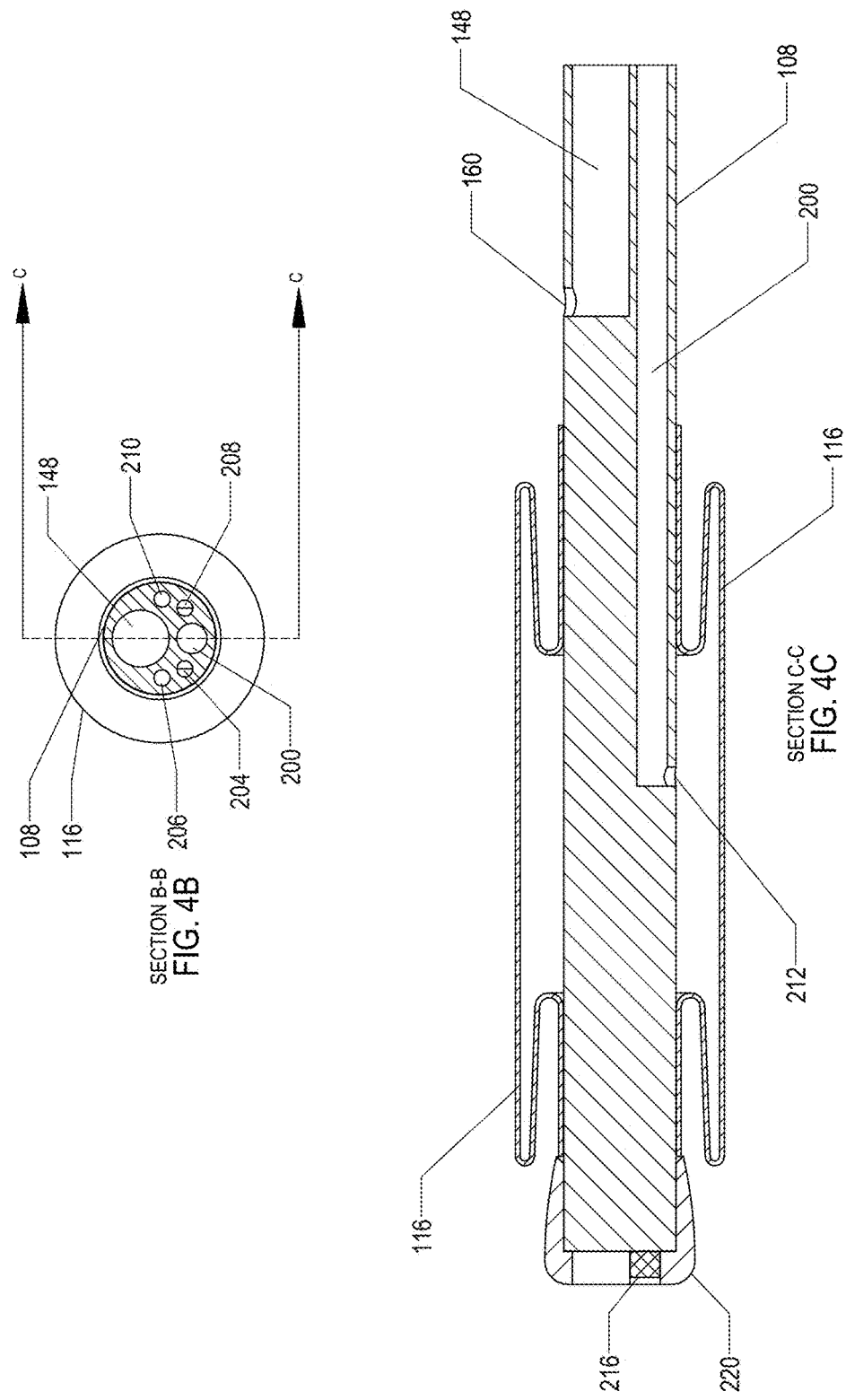

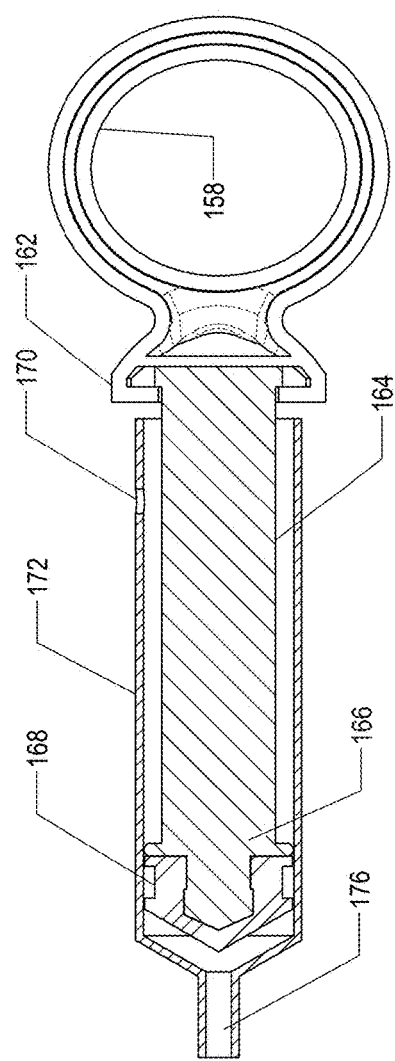
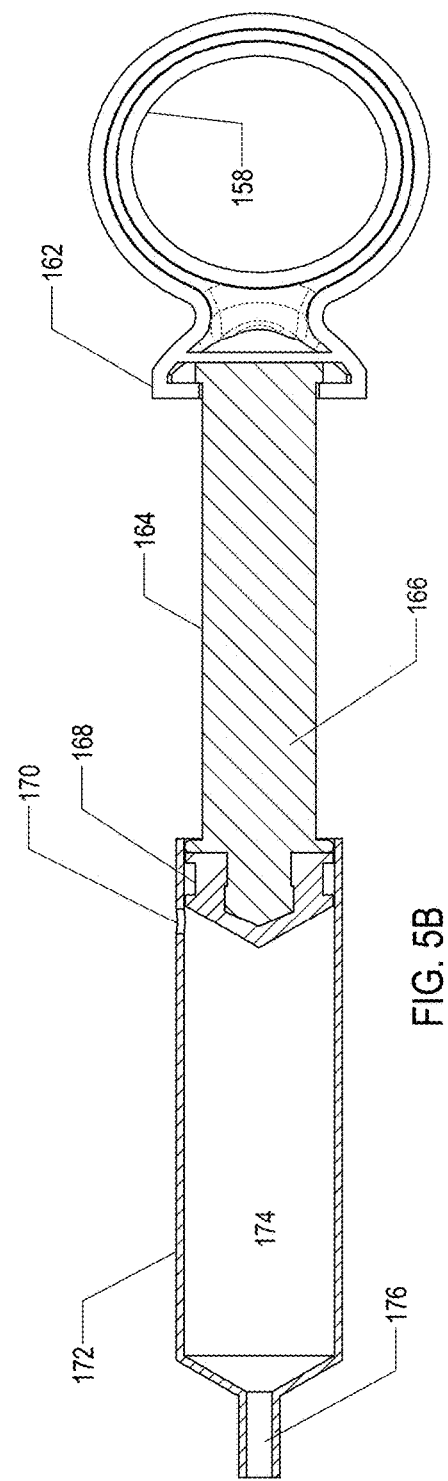
FIG. 5A
FIG. 5B

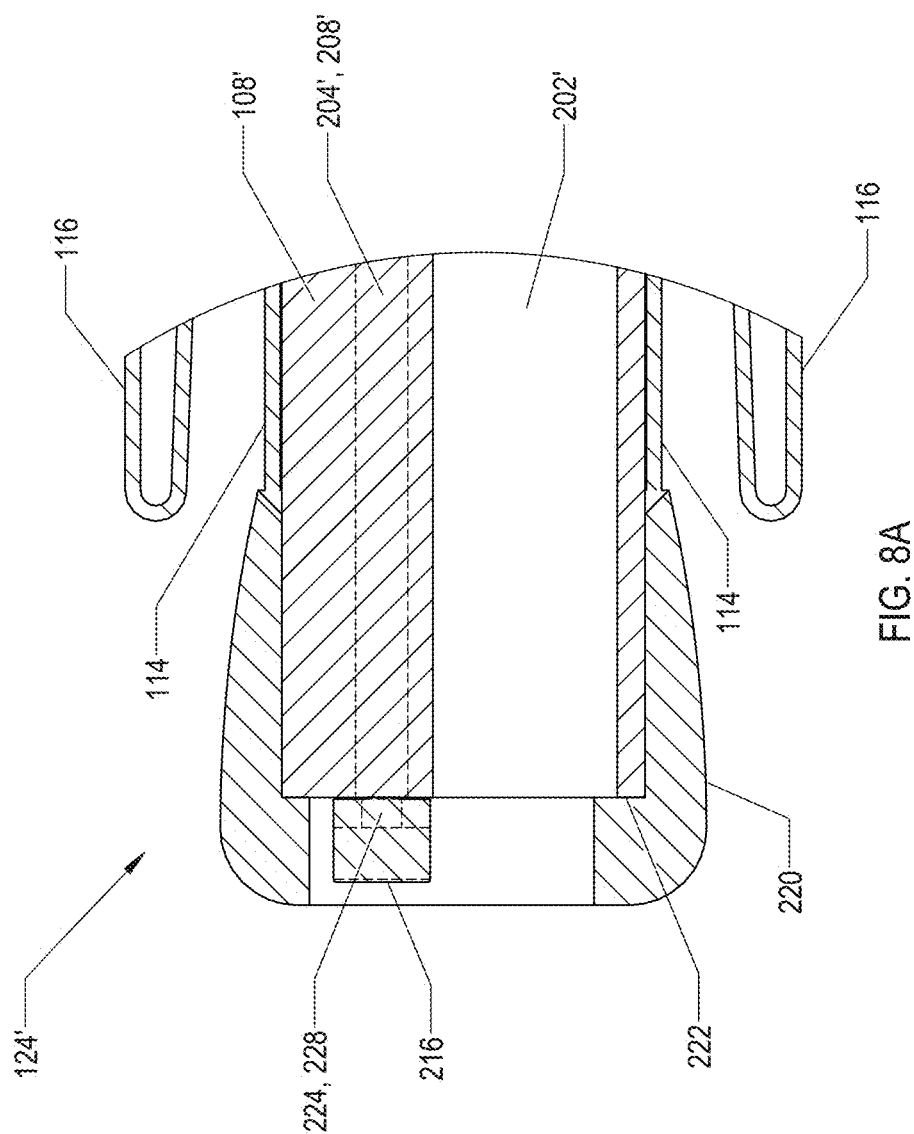

SECTION L-L

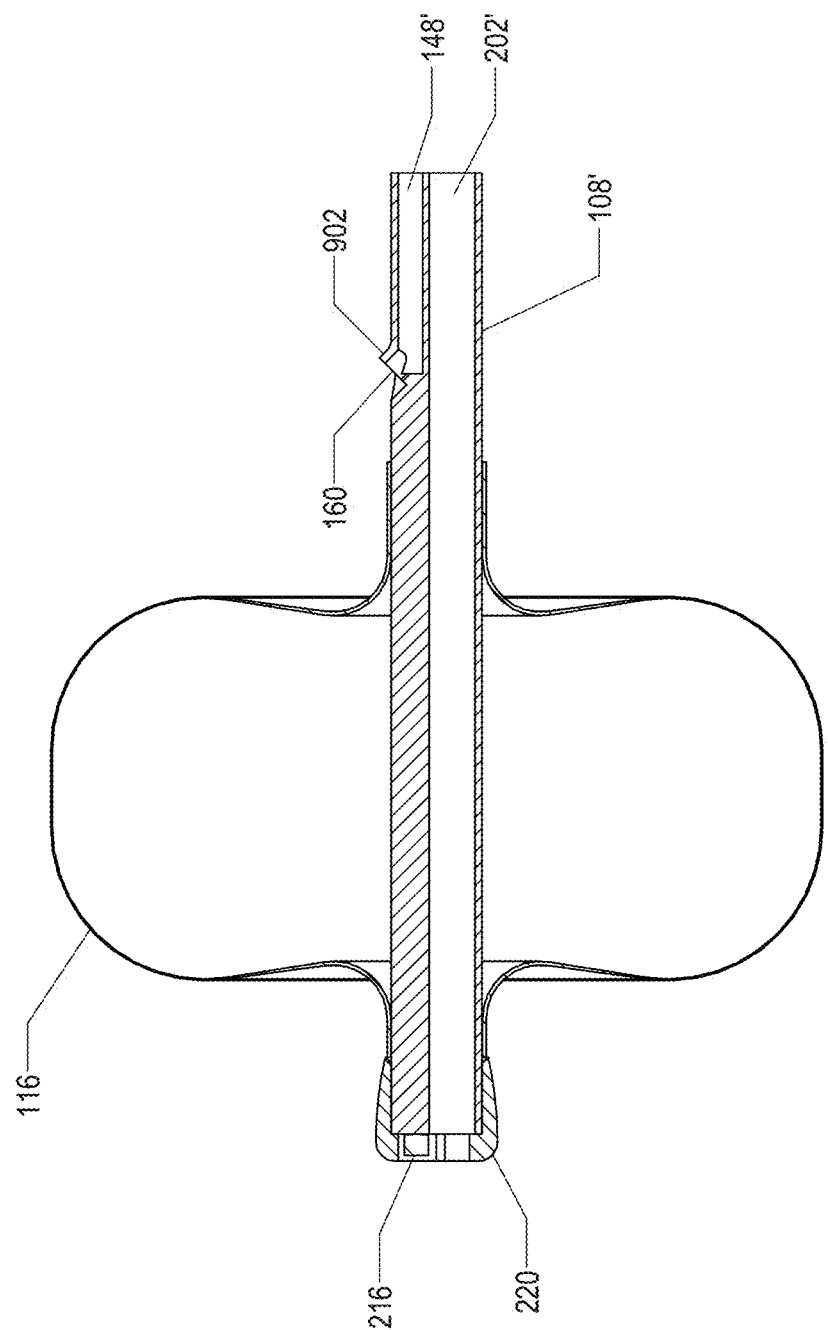

SURGICAL DEVICE FOR PERFORMING A SPHENOPALATINE GANGLION BLOCK PROCEDURE

CROSS REFERENCE TO RELATED APPLICATION

The present application claims the benefit of and priority to, under 35 U.S.C. §119(e), U.S. Provisional Application Ser. No. 61/917,097, filed Dec. 17, 2013, entitled APPARATUS, STSTEM, AND METHOD FOR TREATING HEADACHES, which is hereby incorporated herein by reference in its entirety for all that it teaches and for all purposes.

FIELD OF THE DISCLOSURE

The present disclosure relates generally to devices, methods and systems for treating headaches and cerebral neurovascular disorders, and more specifically, to devices, such as a surgical device, and methods for using such device, for delivering medication to the sphenopalatine ganglion.

BACKGROUND

The sphenopalatine ganglion (SPG) is a collection (or bundle) of nerves that is located in a bony cavity within an individual's skull. The cavity is called the pterygopalatine fossa (or sphenopalatine fossa). There is an SPG and corresponding sphenopalatine fossa located on each side of the skull.

The SPG and sphenopalatine fossa are accessible via an individual's nasal cavity. Individuals who suffer from pain associated with headaches and/or facial aches may elect to undergo a procedure referred to as a sphenopalatine ganglion block, which is a procedure that includes the application of a medication, such as anesthetic, by a trained professional to the SPG. Some of the conventional techniques for performing a sphenopalatine ganglion block procedure, however, are unpleasant to the individual. For example, upon application of the medication to the SPG, a large majority of the medication may flow down the individual's throat. Additionally, the medication is typically distasteful, which further exacerbates the unpleasantness. Furthermore, typical devices used to perform a sphenopalatine ganglion block procedure may not have the ability to accurately locate the SPG without the use of large external imaging systems, such as x-ray systems.

SUMMARY

Accordingly, there is a need for a device, method and/or system such as a surgical device that has the capability to quickly and accurately locate the SPG while performing a sphenopalatine ganglion block procedure, as well as prevent the medication applied to the SPG from flowing down a patient's throat. The present disclosure discusses a method and device that satisfies such needs.

The method may include delivering a medication to a sphenopalatine ganglion of a patient comprising the steps of inserting a device into a nasal cavity of a patient through a nostril, wherein the device comprises a handle comprising a proximal end and a distal end, an inflation device at least partially and integrally disposed within the handle, a flexible tubular member extending from the distal end of the handle, the flexible tubular member comprising a proximal end, a distal end, an inflation lumen coupled to the plunger and extending from the proximal end of the flexible tubular member, and a second lumen extending from the proximal end of the flexible tubular member to a port, an expandable member attached to the flexible tubular member, the expandable member comprising a proximal end and as distal end, wherein the inflation lumen opens into the expandable member, wherein the port is disposed proximally of the proximal end of the expandable member, and an illumination device disposed adjacent the distal end of the flexible tubular member and distally of the expandable member, and activating the illumination device, placing the expandable member adjacent the patient's choana, expanding the expandable member adjacent the patient's choana, introducing a medication to sphenopalatine ganglion through the port in the flexible tubular member, removing at least a portion of the medication from the port in the flexible tubular member, collapsing the expandable member, and removing the device from the nasal cavity.

A device in accordance with this disclosure for accurately locating the SPG, while performing a sphenopalatine ganglion block procedure, and/or for preventing the medication applied to the SPG from flowing down a patient's throat, may include a handle comprising a proximal end and a distal end, an inflation device at least partially and integrally disposed within the handle, a flexible tubular member extending from the distal end of the handle, the flexible tubular member comprising a proximal end, a distal end, an inflation lumen coupled to the plunger and extending from the proximal end of the flexible tubular member, and a second lumen extending from the proximal end of the flexible tubular member to a port, an expandable member attached to the flexible tubular member, the expandable member comprising a proximal end and as distal end, wherein the inflation lumen opens into the expandable member, wherein the port is disposed proximally of the proximal end of the expandable member, and an illumination device disposed adjacent the distal end of the flexible tubular member and distally of the expandable member.

The device may also or alternatively include a switch on the handle for activating the illumination device.

The device may also or alternatively include a pressure relief valve disposed within the handle and coupled to the plunger and the inflation lumen.

Another device for delivering a medication to a patient in accordance with this disclosure may comprise a handle comprising a proximal end and a distal end, an inflation device at least partially and integrally disposed within the handle, a flexible tubular member extending from the distal end of the handle, the flexible tubular member comprising a proximal end, a distal end, an inflation lumen extending from the proximal end, a second lumen extending from the proximal end to a port disposed proximally of the distal end of the flexible tubular member, an expandable member attached to the flexible tubular member, wherein the inflation lumens opens into the expandable member, wherein the port is disposed proximally of the expandable member, and a pressure relief valve disposed within the handle and coupled to the plunger and the inflation lumen.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "medication" shall mean a substance used for medical treatment, such as a medicine or drug or remedy having in a specified formulation. The medicinal substance may also be referred to as a medicament. For the purposes of this disclosure a medication shall include anesthetics, including but not limited to local anesthetics and general anesthetics.

The term "transillumination" shall mean the transmission of light through body tissue, such as the palate (including both the soft palate and hard palate).

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 4B is a cross-sectional end view of the elongated flexible tubular member of the surgical device depicted in FIG. 4 taken along line B-B;

FIG. 4C is a cross-sectional side view of the elongated flexible tubular member depicted in FIG. 4B taken along line C-C;

FIG. 5A is a cross-sectional view of the plunger located within the handle of the surgical device depicted in FIG. 4D, wherein the plunger is illustrated in an extended position;

FIG. 5B is a cross-sectional view of the plunger located within the handle of the surgical device depicted in FIG. 4D, wherein the plunger is illustrated in a retracted position;

FIG. 8A is an enlarged cross-sectional view of an alternative embodiment of the distal end of the elongated flexible tubular member distal of the expandable member of the surgical device depicted in FIG. 4;

FIG. 9 is a cross-sectional side view of an alternative embodiment of the elongated flexible tubular member depicted in FIG. 8C with the expandable member depicted in the expandable state.

Figure 1:
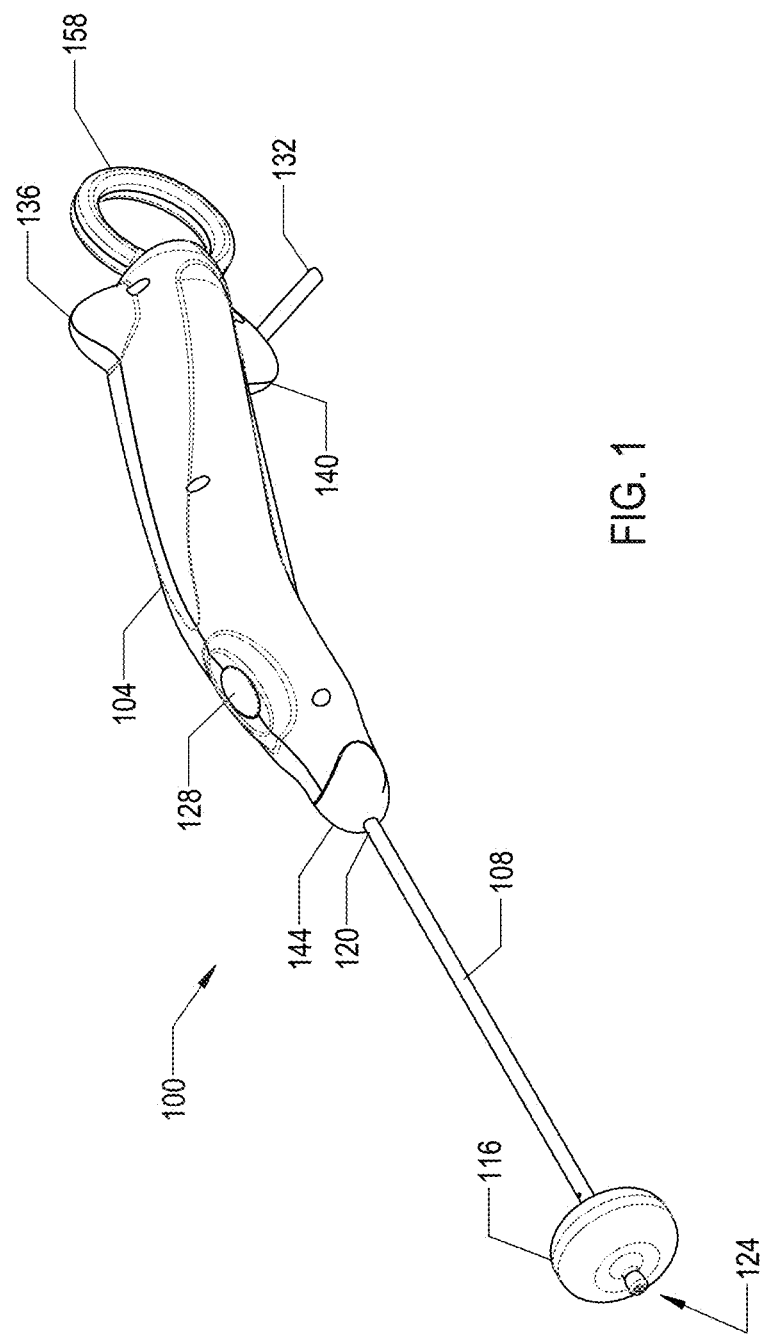
FIG. 1 is a perspective view of an embodiment of a surgical device of the present disclosure.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Embodiments according to this disclosure provide a surgical device that can be deployed safely within a nasal cavity of a patient and apply a medication, such as a local anesthetic, to the patient's sphenopalatine ganglion. FIG. 1-FIG. 4 depict a surgical device 100 having a handle 104 and an elongated flexible tubular member 108. The handle 104, which is ergonomically shaped, includes a proximal end and a distal end 144. The proximal end of the handle includes two projecting abutments 136, 140 so that the user's hand remains comfortably on the handle 104 during use and the user's hand does not slide off the handle 104. It may be preferable for the projecting abutments 136, 140 to be disposed on the top and bottom of the handle such that they are about 180 degrees opposed from one another, as illustrated in the FIGS. 1 & 2, or it may be preferable for the projecting abutments 136, 140 to be disposed in a different orientation with respect to the handle, such as on the sides of the handle 104. It may also be preferable to have less or more than two abutments. For example, it may be preferable to have a continuous abutment around the entire circumference of the handle 104 at or near its proximal end.

Figure 4:
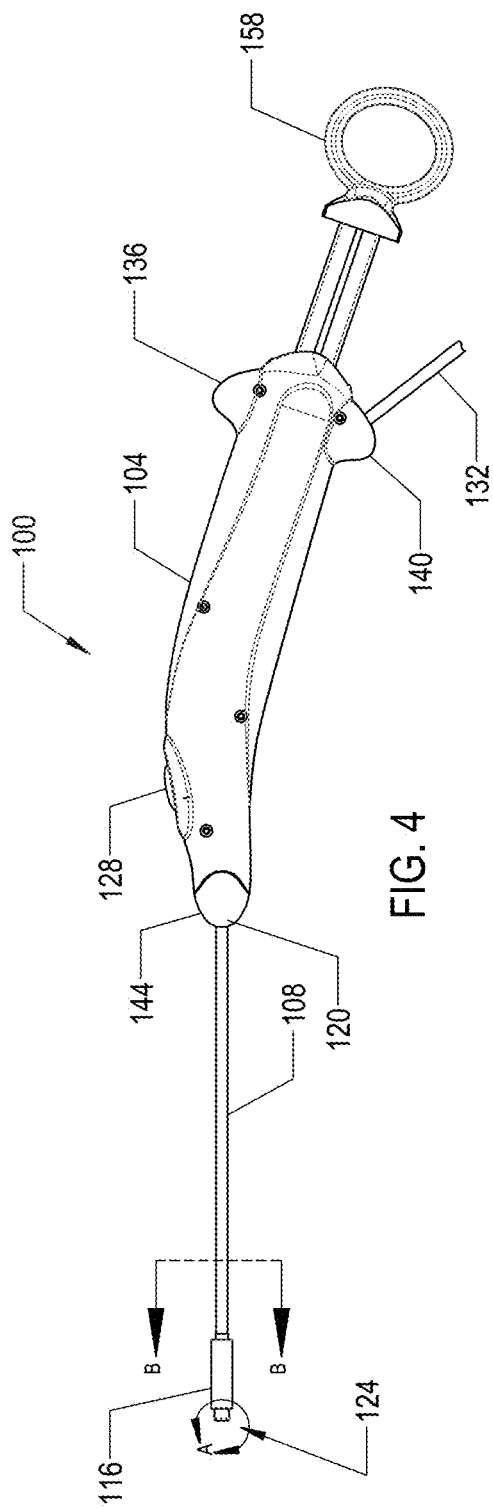
FIG. 4 is a side view of the surgical device depicted in FIG. 2.

As illustrated in FIG. 4, the handle 104 is curved. The proximal portion of the handle 104 has one longitudinal axis and the distal portion of the handle 104 has a different longitudinal axis. The longitudinal axis of the distal portion of the handle 104 may be offset at an angle of about 5 degrees about 60 degrees from the longitudinal axis of the proximal portion of the handle 104. It may be preferable for the offset angle to be about 10 degrees about 45 degrees and even more preferable for the offset angle to be about 20 degrees to about 30 degrees. The longitudinal axes of the proximal and distal portions of the handle 104 smoothly intersect, thereby creating a handle with a curved profile. The distal end 144 of the of the handle portion 104 may also have a rounded configuration, which is more ergonomic to engage the patient's nostril(s) upon insertion of the device 100, namely the elongated flexible tubular member 108, thereto.

Figure 2:
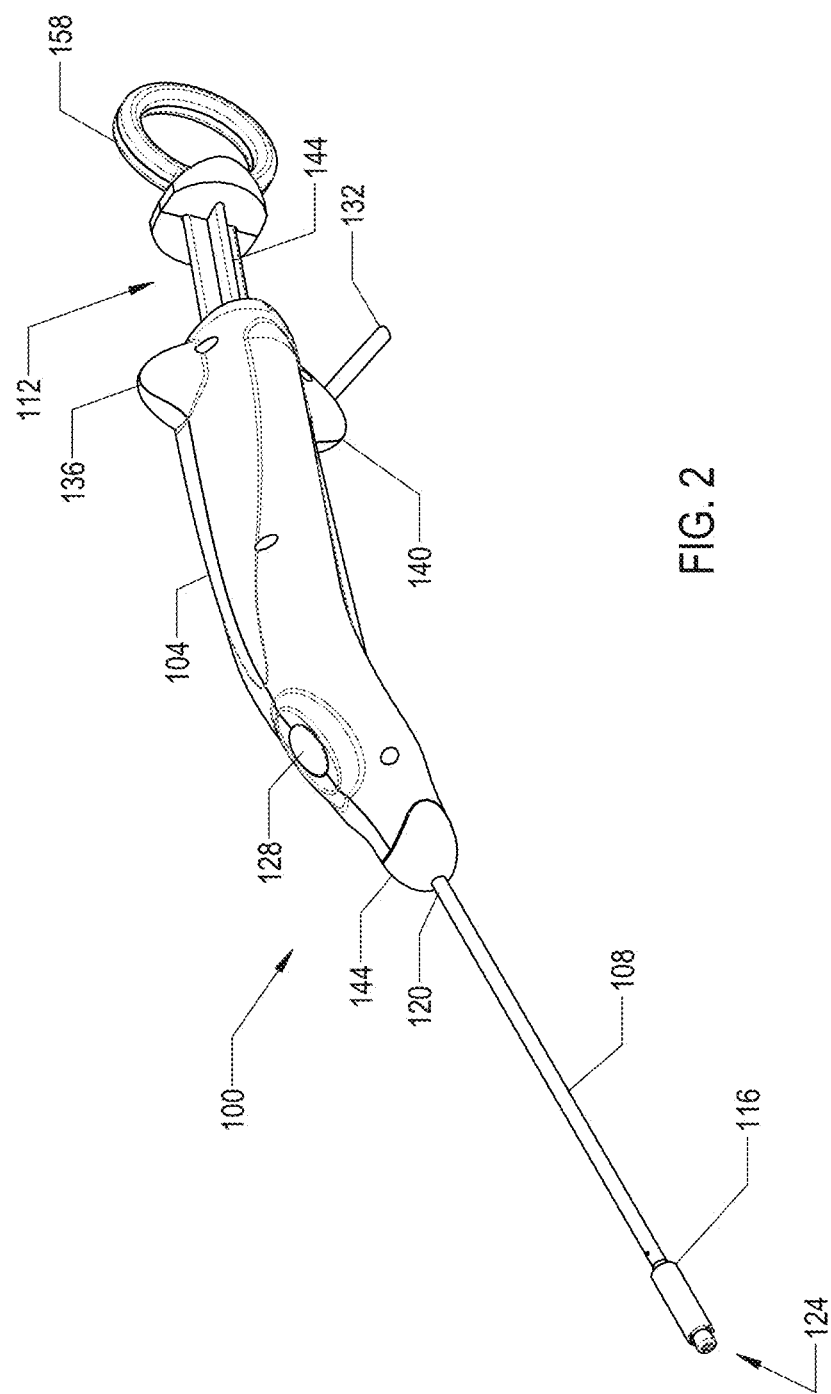
FIG. 2 is an alternate perspective view of the surgical device depicted in FIG. 1.
Figure 3:
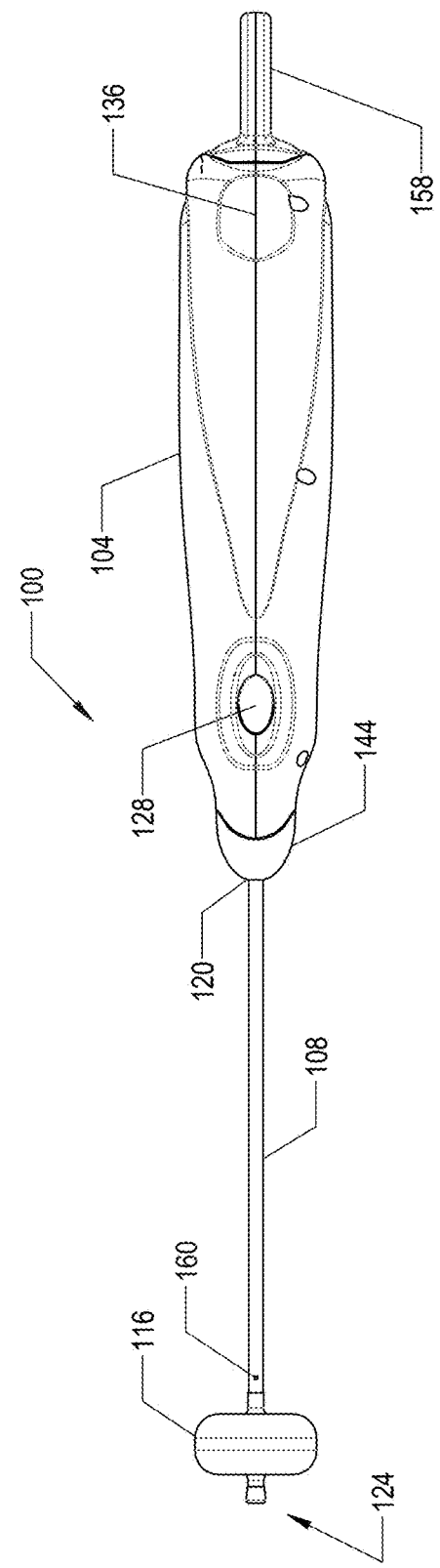
FIG. 3 is a top view of the surgical device depicted in FIG. 1.

The elongated flexible tubular member 108 includes a proximal end 120, which is attached to the distal end of the 144 of the handle 104. An expandable member 116, such as a balloon, is located at, adjacent to or toward the distal end 124 of the flexible tubular member 108. FIGS. 1 & 3 depict the expandable member 116 in an inflated state, and FIGS. 2 & 4 depict the expandable member 116 in a deflated state. The shape and size of the expandable member 116 may differ depending upon the patient's anatomy. For example, the size of the expandable member 116 may be smaller for children and larger for adults. It may be preferable for the expandable member 116 to have an inflated diameter of about 1 cm to 4 cm, with a possible preferential diameter of about 2.5 cm, and an inflated length of about 1 cm to 3, with a possible preferential inflated length of about 2.5 cm.

As discussed in more detail below, the handle 104 includes an inflation device, such as a syringe 112, integrated therein. The syringe 112 comprises a barrel 172, a plunger 164 at least partially disposed within the barrel 172, and a distal tip 176 at the end of the barrel 172. When the plunger 164 is depressed, the expandable member 116 is expanded (inflated) with fluid, such as air, and when the plunger 164 is refracted, the expandable member 116 is collapsed (deflated). It shall be understood that either a pneumatic inflation device, which utilizes air as the fluid, or a hydraulic inflation device, which utilizes liquid (e.g., saline, water, etc.) as the fluid, can be used.

The handle 104 also includes a switch 128 for activating an illumination device 216, such as a light-emitting diode (LED) disposed at or toward the distal end 124 of the elongated flexible tubular member 108. The switch 216 activates a power source, such as a battery, that is coupled to the illumination device 216 by two or more conductors (e.g., wires) 224, 228. The wires 224, 228 are disposed within lumens 224, 228 that travel from the proximal end to the distal end of the elongated flexible tubular member 108. As discussed above, the expandable member 116 is also disposed at or near or toward the distal end 124 of the elongated flexible tubular member 108. It is preferable for the illumination device 216 to be disposed distally of the expandable member 116 along the elongated flexible tubular member 108, thereby allowing the illumination device 216 to project light in a manner that is unobstructed by the expandable member 116. That is, it is preferable for the expandable member 116 to be disposed proximally of the illumination device 216 along the elongated flexible tubular member 108. For example, it may be preferable for the distal end of the expandable member 116 to be disposed about 0 to 1 mm and potentially even more preferable to be disposed at the distal end 124 of the elongated flexible tubular member 108.

Figure 4A:
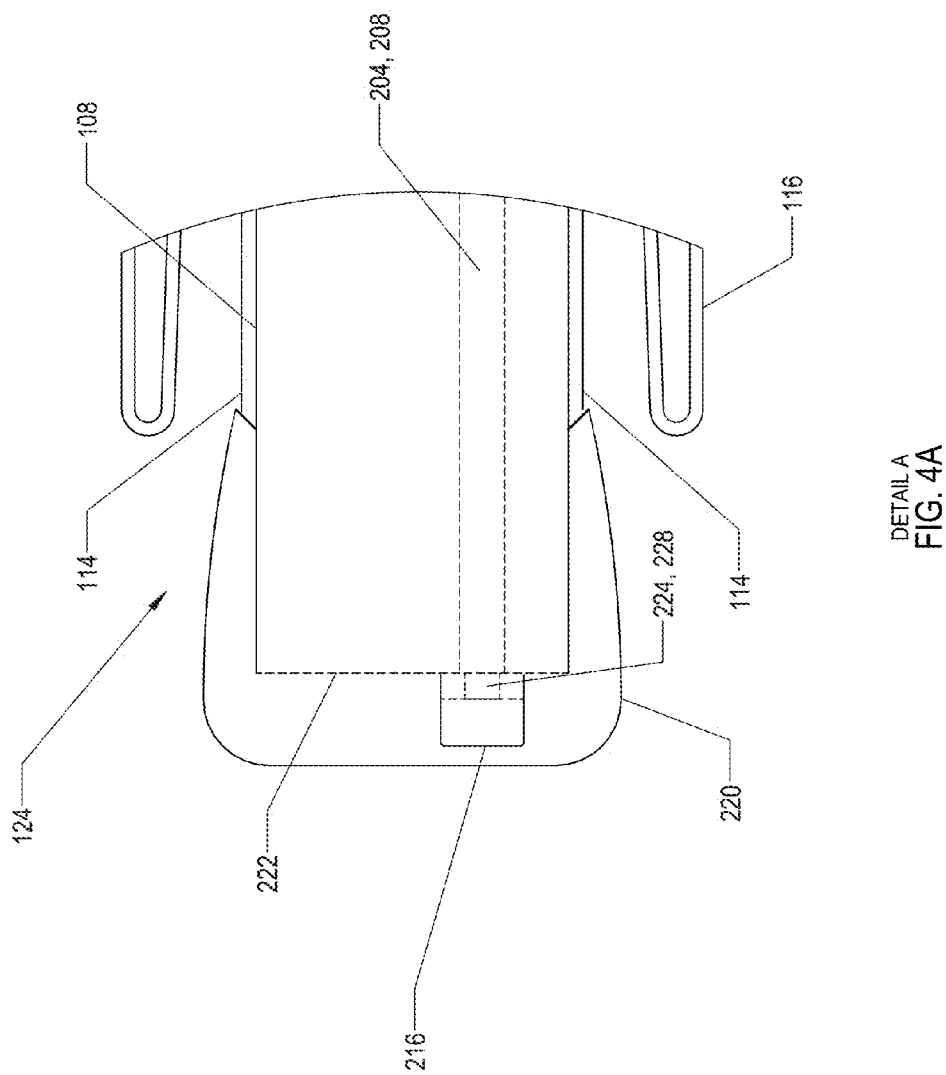
FIG. 4A is an enlarged cross-sectional view of the distal end of the elongated flexible tubular member distal of the expandable member of the surgical device depicted in FIG. 4.

Referring to FIG. 4, there is depicted a side view of an embodiment of the surgical device 100 of the present disclosure. FIG. 4A is an enlarged cross-sectional view of the distal end 124 of the elongated flexible tubular member 108 illustrating a portion of the expandable member 116 in a deflated state. The distal end 124 of the elongated flexible tubular member 108 includes a cover 220 coupled to it. The cover 220 is constructed of a transparent material, such as polycarbonate. The cover 220 protects the illumination device 216. The cover 220 may also be shaped such that its edges are curved, thereby providing an atraumatic end to the surgical device. The cover 220 can be coupled directly to the distal face 222 of the elongated flexible tubular member 108 and/or it can be coupled to the perimeter of the distal end 124 of the elongated flexible tubular member 108. The tip 220 may preferably be coupled to the distal end 124 of the elongated flexible tubular member 108 by an adhesive compound. Alternative means of coupling the tip 220 to the distal end 124 of the elongated flexible tubular member 108 includes mechanical means, such as pressed fittings, snap on fittings, or a threaded arrangement between the tip 220 and the elongated flexible tubular member 108.

Continuing to refer to FIG. 4A, there is depicted an illumination device 216, which is also coupled to the distal face 222 of the elongated flexible tubular member 108 such that the illumination device projects light distally of the elongated flexible tubular member 108. Similar to tip 220, the illumination device 216 is coupled to the distal end 124 of the elongated flexible tubular member 108 by an adhesive. It may also be preferable for the tip 220 to surround at least a portion of the illumination device 216, thereby protecting the illumination device 216. The illumination device is powered by a power source, such as a battery, via one or more wires 224, 228 that couple the power source to the illumination device 216. The wires 224, 228 are disposed within lumens 224, 228 that travel from the proximal end to the distal end of the elongated flexible tubular member 108.

Referring to FIG. 4B, there is depicted a cross-sectional view of the elongated flexible tubular member 108 of the surgical device 100 depicted in FIG. 4 taken along line B-B. The elongated flexible tubular member 108 comprises a plurality of lumens. Although a different number of lumens may be used, FIG. 4B illustrates four lumens: lumen 148 is used to transport the medication to/from the medication port 160 located proximally of the expandable member 116; lumen 200 is used to transport fluid (e.g., air, water, saline, etc.) to/from the inflation port, which open into the expandable member 116; and two lumens 204, 208 provide channels for the wires 224, 228 to travel. All four lumens 148, 200, 204 & 208 have openings at the proximal end of the elongated flexible tubular member 108. Not all four lumens, however, may have openings at the distal end of the elongated flexible tubular member 108. For example, the lumen 148 used to transport the medication may have an opening at the proximal end of the elongated flexible tubular member 108 and an opening (or port) at 160, which is located proximally of the expandable member 116. Additionally, the lumen 200 used to transport fluid to inflate the expandable member 116 may have a have an opening at the proximal end of the elongated flexible tubular member 108 and an opening (or port) at 212, which opens into the expandable member 116. Lumens 204, 208 may have an opening at the proximal end of the elongated flexible tubular member 108 and an opening at or near the distal end of the elongated flexible tubular member 108, thereby allowing the wires 224, 228 to travel all or the majority of the length of the elongated flexible tubular member 108 to the illumination device 216.

Alternatively, the elongated flexible tubular member 108 may not have lumens 204, 208. For example, if the elongated flexible tubular member 108 is constructed (e.g., molded) in a manner such that the wires 224, 228 are integral with the elongated flexible tubular member 108, then lumens 204, 208 may not be needed. Additionally, the elongated flexible tubular member 108 may have additional lumens 206, 210.

Figure 8B:
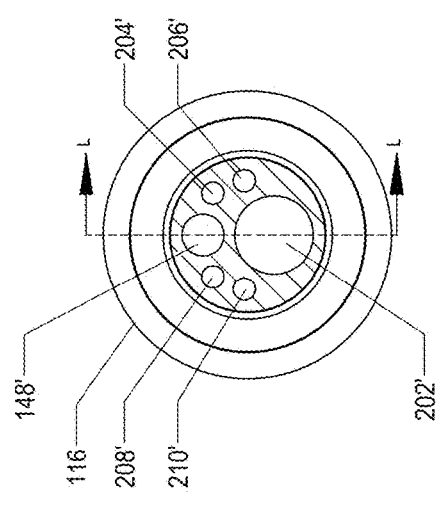
FIG. 8B is a cross-sectional end view of an alternative embodiment of the elongated flexible tubular member of the surgical device depicted in FIG. 4 taken along line B-B.
Figure 8C:
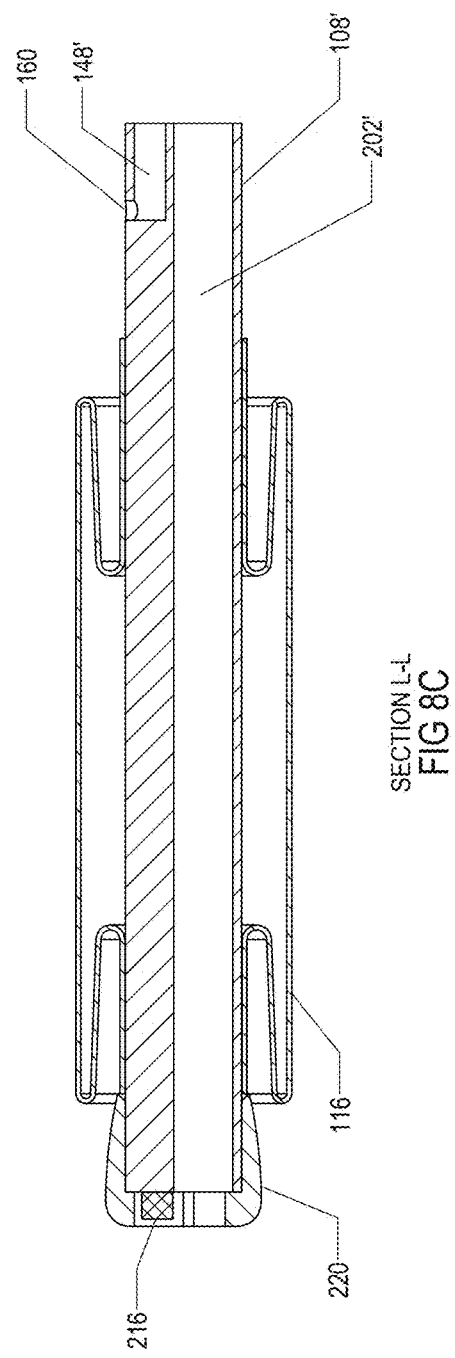
FIG. 8C is a cross-sectional side view of the elongated flexible tubular member depicted in FIG. 8B taken along line C-C.

Another alternative embodiment may include an additional lumen in the elongated flexible tubular member 108 through which an imaging device may be inserted or incorporated. For instance, the surgical device 100 may include a reusable endoscope that is inserted through an opening (not shown) in the handle 104 and travels through the additional lumen in the elongated flexible tubular member 108 such that the endoscope is adjacent the illumination device 216 in the cover 220. Referring to FIGS. 8A, 8B & 8C, there is depicted such an alternative embodiment of the flexible tubular member 108' that includes lumen 202', which extends from the proximal end to the distal end of the flexible tubular member 108', and is configured to have an endoscope or other imaging device inserted thereto. Lumen 148' will be used to transport the medication to/from the medication port 160' located proximally of the expandable member 116; two lumens 204, 208 provide channels for the wires 224, 228 to travel to/from the illumination device 220; lumen 206' is used to transport fluid (e.g., air, water, saline, etc.) to/from the inflation port, which open into the expandable member 116; and lumen 208' is an additional lumen. Although it is not shown in the figures, it may also be desirable for the cover and/or the distal end of the flexible tubular member to have an optical divider that separates the light emitted by the illumination device from directly entering the endoscope or imaging device.

Regarding the placement of the opening 160 for delivering the medication, it may be preferable for the opening 160 to be disposed about 1 mm to 10 mm from the proximal end of the expandable member 116 and possibly more preferably to be disposed about 2 mm to 5 mm from the proximal end of the expandable member 116. Locating the opening 160 proximally of the proximal end of the expandable member 116 allows the medication to collect within the nasal cavity above the expandable member 116, while the expandable member 116 is inflated. It may be preferable for the medication to collect within the nasal cavity and form a pool of medication such that the level of medication rises to sphenopalatine fossa and/or the mucosa overlaying the SPG. Depending upon the size of the patient's nasal cavity, the volume of medication introduced to the nasal cavity and used to create such a pool may be between 2 milliliters to 15 milliliters, and potentially preferable for about 5 milliliters to 10 milliliters.

Figure 4D:
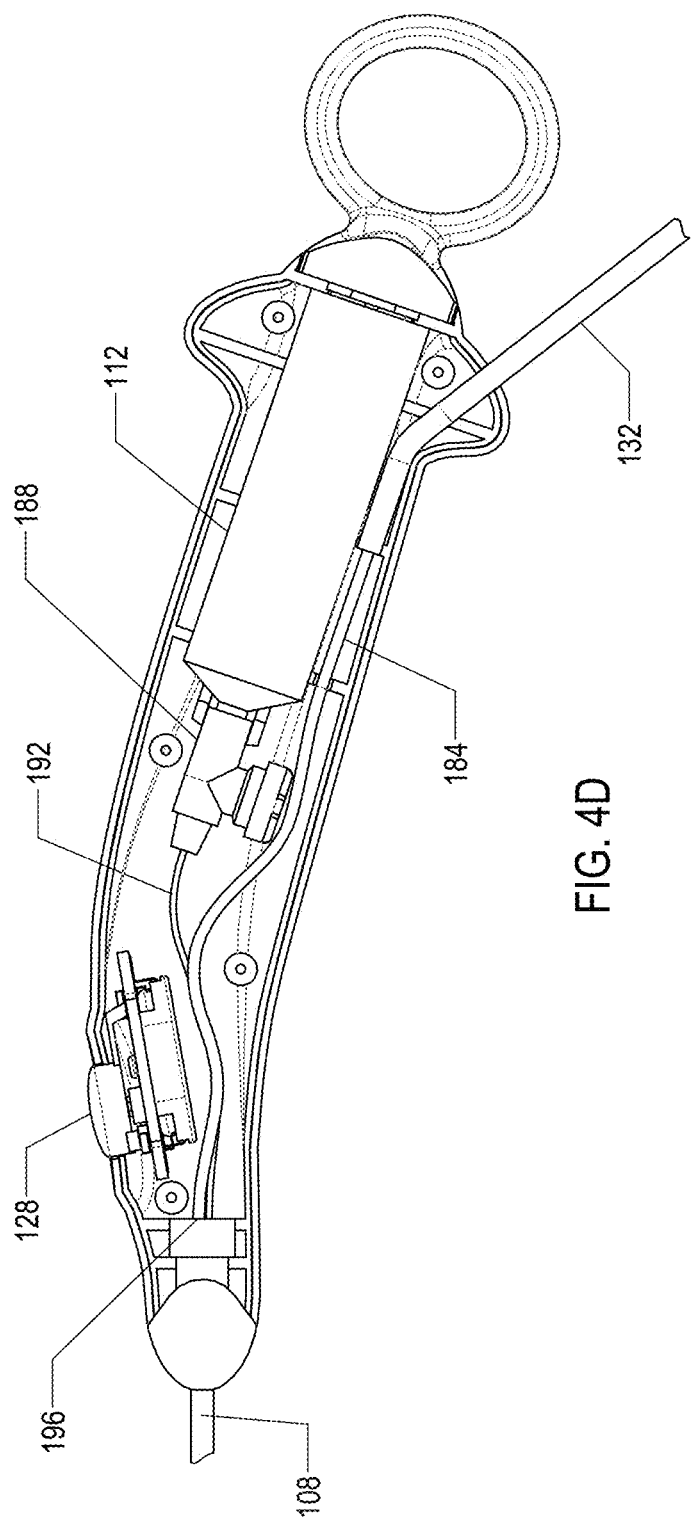
FIG. 4D is a cross-sectional view of the handle of the surgical device depicted in FIG. 4.

Referring to FIG. 4D, FIG. 5A and FIG. 5B, an inflation device, such as a syringe 112, is integrated into the handle 104. The syringe 112 is used to inflate and deflate the expandable member 116. Integrating the inflation device in the handle 104 reduces the likelihood of a clinician confusing which port(s) to connect the devices (i.e., syringes) used to introduce the medication and the inflation fluid. That is, by including an inflation device, such as the syringe 112, in the handle 104, a clinician will know and/or be instructed to use the integrated syringe 112 to inflate the expandable member 116 and an external syringe (not shown) to introduce the medication. Stated differently, a clinician will only have to introduce one fluid, namely the medication, through an external syringe, thereby reducing potential confusion as to which fluid to introduce and/or into which port. Alternatively, the syringe used to introduce the medication may be integrated into the handle 104 in lieu of the syringe 112 used to inflate and deflate the expandable member 116. A further alternative embodiment may include a handle 104 with two clearly marked integrated syringes—one syringe for the medication and another syringe for the inflation fluid.

The syringe 112 comprises a barrel 172, a plunger 164 at least partially disposed within the barrel 172, and a distal tip 176 having an opening at the distal end of the barrel 172. The plunger 164 has a shaft portion 166 and a proximal end 162 and distal end 168 at the respective ends of the shaft portion 166. The proximal end 162 and a distal end 168 may be coupled to the shaft portion 166 or be integrally formed thereto. The proximal portion 162 may also have a handgrip or finger grip, such as a ring 158, for a clinician to ergonomically and comfortably depress and retract the barrel 172. When the plunger 164 is depressed, the expandable member 116 is inflated, and when the plunger 164 is retracted, the expandable member 116 is deflated.

It may also be preferable for the barrel 172 to have an opening (port) 170 adjacent, at or toward its proximal end. When the surgical device 100 is manufactured, it is assembled and/or packaged at a certain atmospheric pressure depending upon the geographic location of the manufacturing and/or packaging facility. The atmospheric pressure of the surgical site where the surgical device 100 is used, however, may be different than that at the manufacturing and/or packaging facility. Including the opening 170 within the barrel 172 allows the pressure within barrel to equalize with the pressure of the surgical site prior to use. It may also be preferable to ship the surgical device 100 in a configuration such that the plunger 164 is in a partially or fully retracted position such, thereby allowing the opening 170 to be located distally of the distal end 168 of the plunger 164. Shipping the surgical device in this configuration may enhance the time for the pressure within the chamber of the barrel to equalize with the atmospheric pressure at the surgical site more quickly.

During use of the surgical device 100, clinicians may also repeatedly depress and retract the plunger 164. Such repeated action has the potential to overinflate the expandable member 116. Inclusion of the opening 170 within the barrel 172 allows the pressure within barrel's chamber 174 to equalize with the atmospheric pressure upon retraction of the plunger 164, thereby reducing the likelihood of overinflating the expandable member 116. That is, upon depression of the plunger 164, the pressure within the chamber 174, as well as the pressure within the expandable member 116, increases above atmospheric pressure at the surgical site. Upon each retraction of the plunger 164, the pressure within the chamber 174, as well as the pressure within the expandable member 116, decreases back to atmospheric pressure prior to another depression of the plunger 164 because the fluid within the chamber 174 is vented to the atmosphere via the opening 170.

Venting the fluid within the chamber 174 also allows the expandable member 116 to deflate (or further deflate) upon application of pressure to the exterior of the expandable member 116. For example, upon retraction of the plunger 164, the pressure within the expandable member 116 may not immediately cause the expandable member 116 to completely deflate. That is, the expandable member 116 may retain a certain amount of fluid after retraction of the plunger, thereby allowing the expandable member 116 to remain partially inflated. Accordingly, when the surgical device 100, including the expandable member 116, is initially removed from the patient's nasal cavity, the expandable member 116 may be partially inflated. Inclusion of opening 170 within chamber 174 allows the expandable member 116 to further deflate upon removal of the surgical device 100, including the expandable member 116, from the patient's nasal cavity. Allowing the expandable member 116 to further deflate upon removal of the surgical device 100 assists in reducing the likelihood of the expandable member 116 causing discomfort to the patient.

Continuing to refer to FIG. 4D, a pressure relief valve 188 is disposed between the syringe 112 and the expandable member 116. Inclusion of the pressure relief valve 188 into the inflation circuit reduces the possibility of over pressurizing and over expanding the expandable member 116, particularly during a clinician's repeated depression and retraction of the plunger 164. The pressure relief valve 188 is a valve used to control or limit the pressure in a circuit, such as the inflation circuit. The pressure is relieved by allowing the pressurized fluid (e.g., air) to flow to an auxiliary passage, preferably in the valve, out of the circuit. The pressure relief valve is designed or set to open at a predetermined set pressure to protect the expandable member 116 from being subjected to pressures that exceed the desired clinical limits. When the set pressure is exceeded, the pressure relief valve is forced open and a portion of the fluid is diverted through the auxiliary route vented to the atmosphere. As the fluid is diverted, the pressure inside the circuit decreases. Once the pressure within the pressure relief valve reduces back to or below the predetermined set pressure, the valve will close. For example, the predetermined set pressure may be set between about 5 psi (0.345 bar) to 15 psi (1.034 bar) or possibly between about 8 psi (0.552 bar) to 12 psi (0.827 bar) or nominally about 10 psi (0.690 bar).

The pressure relief valve 188, particularly the proximal end of the pressure relief valve 188, is coupled to the distal tip 176 of the syringe 112. The distal end of the pressure relief valve 188 is, in turn, coupled to the tube 192 that is coupled to the inflation lumen 148 in the elongated flexible tubular member 108. Alternatively, the tube 192 may be omitted by directly coupling the distal end of the pressure relief valve 188 to the inflation lumen 148 in the elongated flexible tubular member 108.

FIG. 4D also illustrates a female luer adaptor 132 attached to the surgical device 100. The female luer adaptor 132 allows a clinician to connect an auxiliary syringe (not shown) having a male luer the mates with the female luer adaptor 132. The auxiliary syringe will include the medication that is introduced through the surgical device 100 proximal of the expandable member to the mucosa overlaying the SPG. Upon actuation (e.g., depression) of the auxiliary syringe, the medication travels from the auxiliary syringe to the female luer adaptor 132 through a tube 184 to the medication lumen 200 and eventually to opening 160. Alternatively, the tube 184 may be omitted by directly coupling the female luer adaptor 132 to the medication lumen 200.

Regardless of whether a tube 184 is included, the medication is preferably introduced through the surgical device 100 after the expandable member 116 is expanded because expanding the expandable member 116 reduces the likelihood of the medication from flowing down the patient's throat. As discussed above, after the medication is introduced into the nasal cavity through opening 160, the medication collects within the nasal cavity above the expandable member, when the expandable member 116 is expanded adjacent the choana. It may be preferable for the medication to collect within the nasal cavity and form a pool of medication such that the level of medication rises to sphenopalatine fossa and/or the mucosa overlaying the SPG. Once the desired medication level is attained, it may be desirable for the medication to remain in the patient's nasal cavity for a period of time to maximize the medication's exposure to the mucosa overlaying the SPG and the SPG itself. For example, it may be desirable for the medication to remain in the patient's nasal cavity at a level to overlay the mucosa of the SPG, for a period of time from about 5 minutes to 35 minutes, including any time interval (e.g., 1 minute, 2 minutes, 3 minutes, 4 minutes, 5 minutes, etc.) there between. It may be more desirable for such time period to be about 10 minutes to 30 minutes, and even more desirable for such time period to be about 15 minutes to 25 minutes, and even further desirable for such time period to be about 20 minutes.

To assist in maintaining the preferable level of medication for the desired time period, the auxiliary syringe may remain connected to the female luer adaptor 132 during such time period. After the medication has contacted the mucosa and the SPG for a sufficient period, the clinician may retract the auxiliary syringe, thereby removing some or all of the medication from the patient's nasal cavity through the same opening 160 used to introduce the medication. That is, by retracting the syringe, a negative pressure or suction force is created in the medication circuit, thereby pulling the medication located within the patient's nasal cavity through the opening 160 and back into the same or different auxiliary syringe. After the medication is withdrawn from the patient's nasal cavity, the expandable member 116 is collapsed, and the surgical device 100 may be removed. As discussed in more detail below, the benefit of including the expandable member 116 with the surgical device 100 allows the clinician to create a blockage within the patient's throat and fill a portion of the nasal cavity such that medication directly contacts the mucosa overlaying the SPG for a sustained period while preventing the medication from flowing down the patient's throat.

Figure 6A:
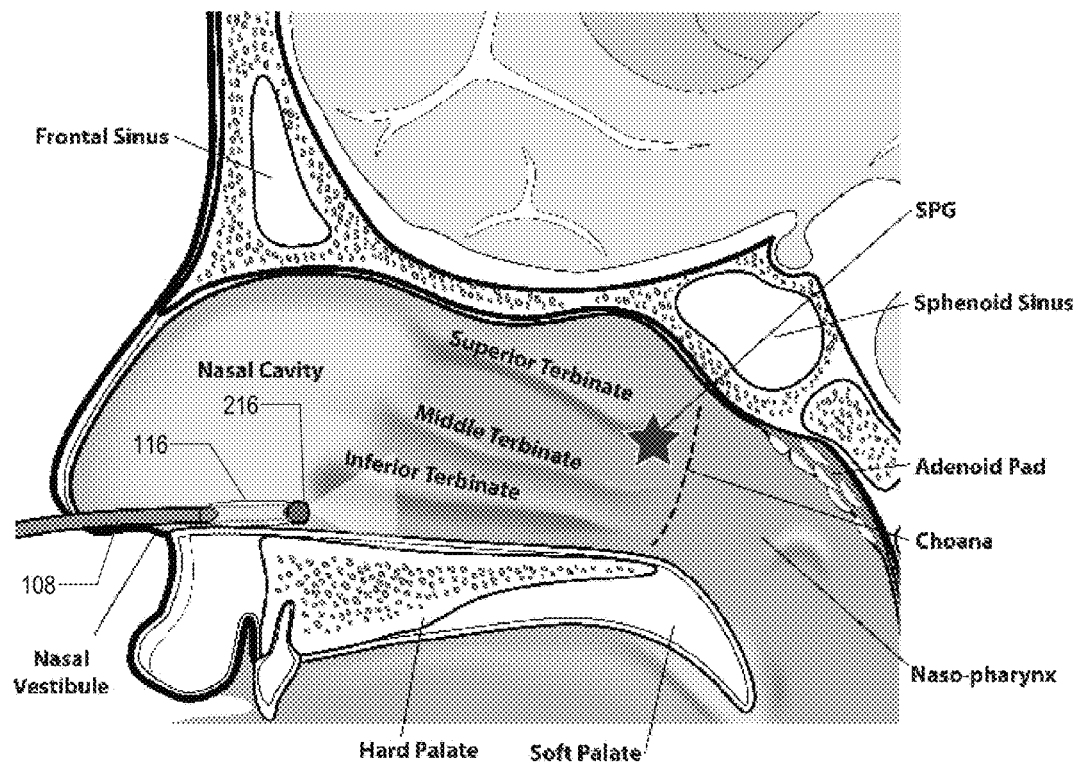
FIG. 6A is a cross-sectional view of a patient's head with an embodiment of a surgical device of the present disclosure, with the expandable member in a deflated state, entering the patient's nasal cavity.
Figure 6B:
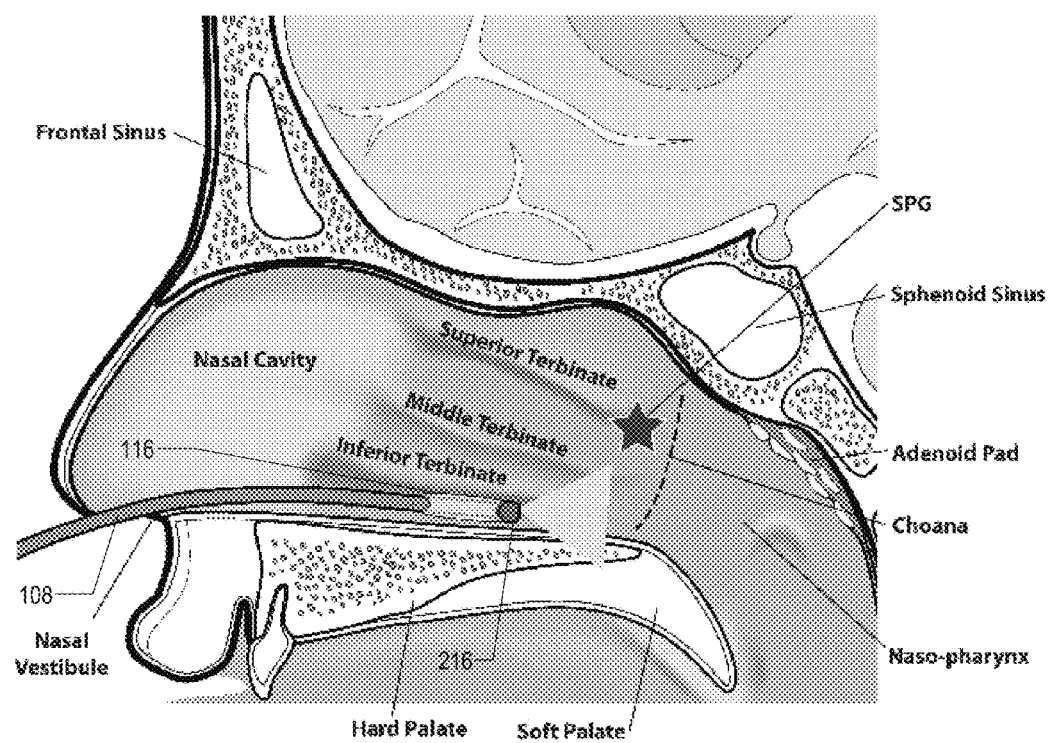
FIG. 6B is a cross-sectional view of a patient's head with an embodiment of a surgical device of the present disclosure, with the expandable member in a deflated state, located in the patient's nasal cavity.
Figure 6C:
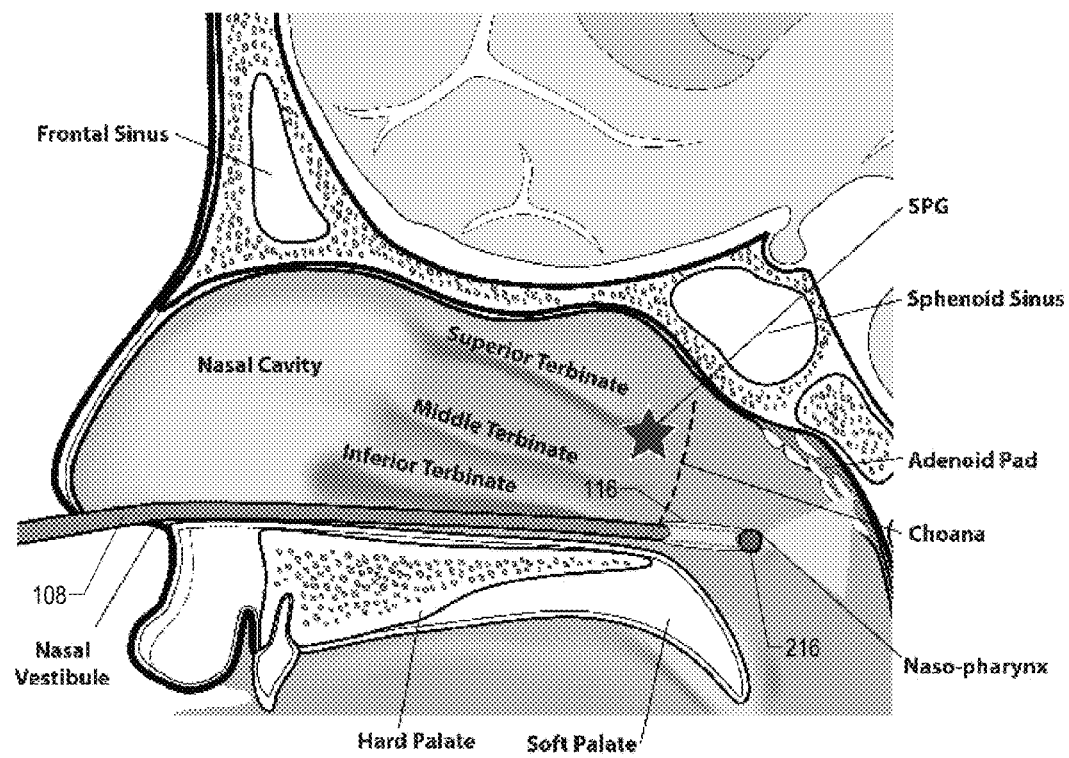
FIG. 6C is a cross-sectional view of a patient's head with an embodiment of a surgical device of the present disclosure, with the expandable member in a deflated state, located in the patient's nasal cavity with the expandable member disposed adjacent the choana.
Figure 6D:
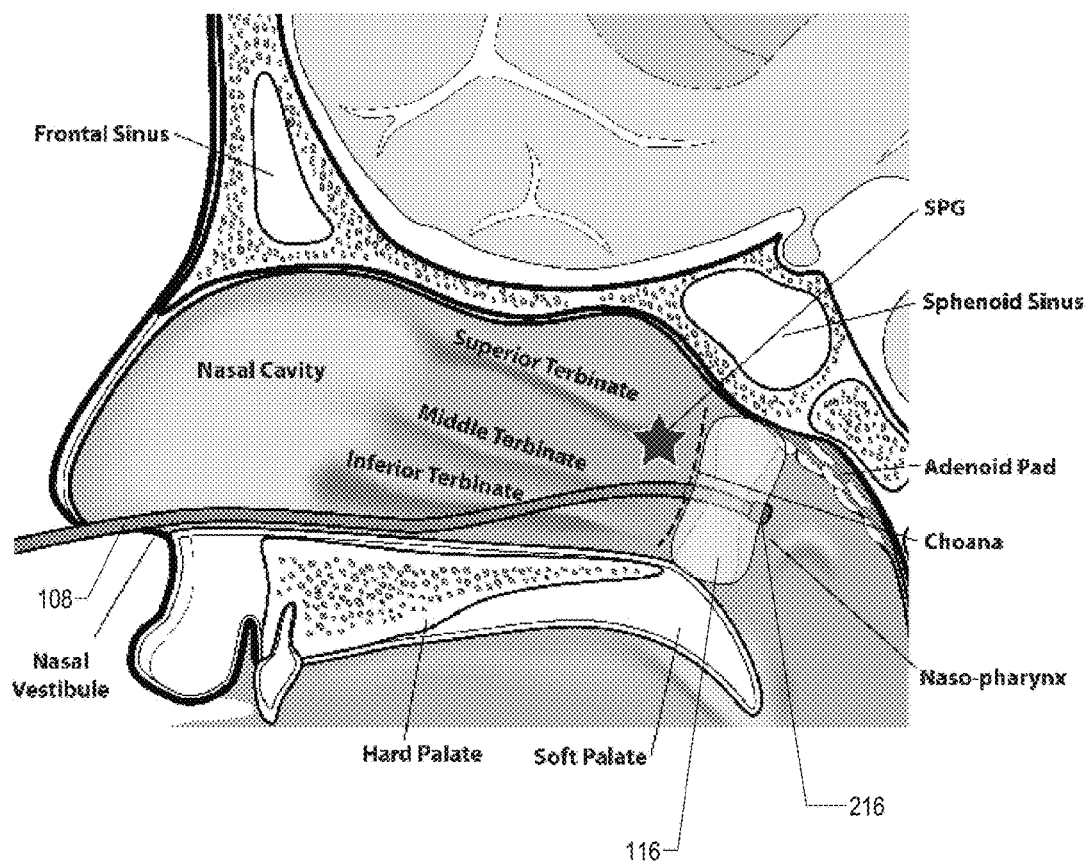
FIG. 6D is a cross-sectional view of a patient's head with an embodiment of a surgical device of the present disclosure, with the expandable member in an inflated state, located in the patient's nasal cavity with the expandable member disposed adjacent the choana.
Figure 6E:
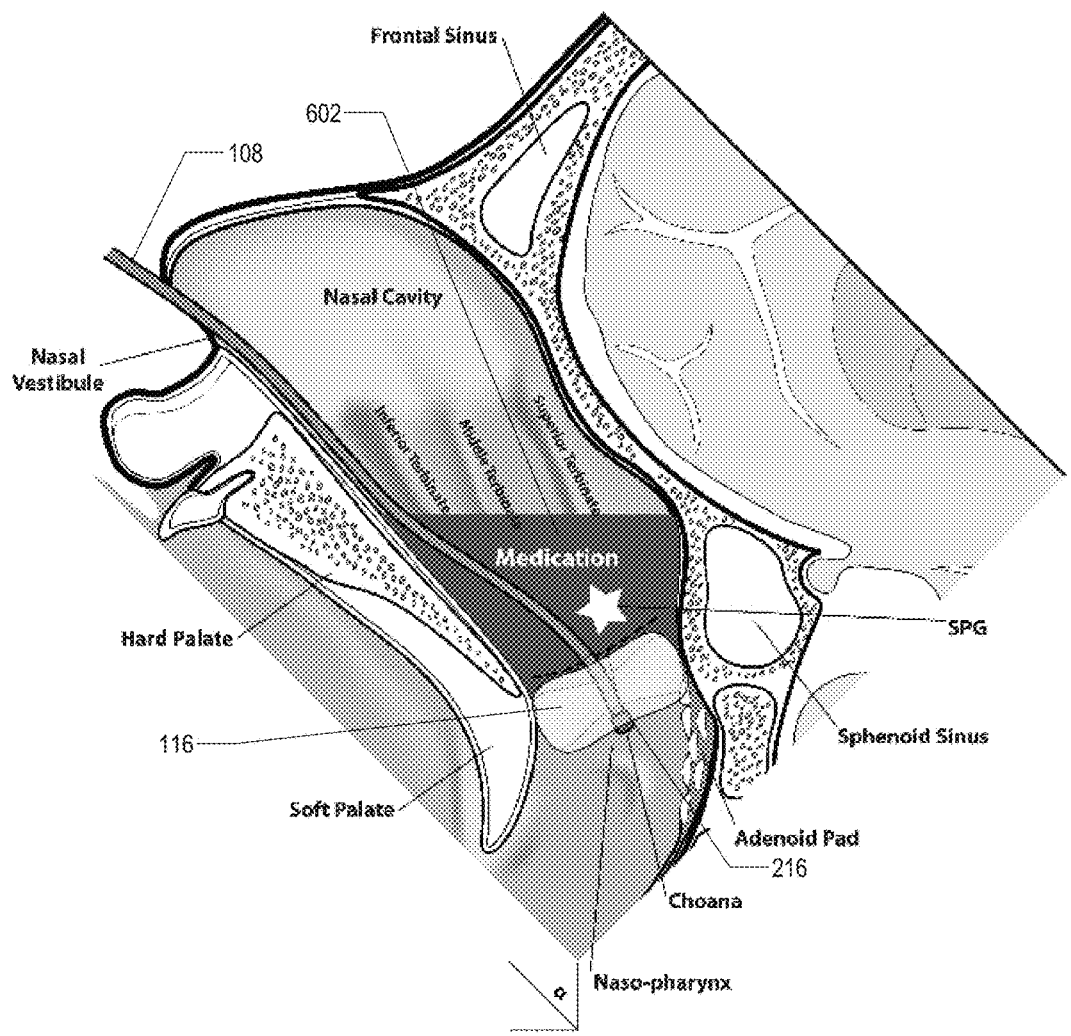
FIG. 6E is a cross-sectional view of a patient's head with an embodiment of a surgical device of the present disclosure, with the expandable member in an inflated state, located in the patient's nasal cavity with the expandable member disposed adjacent the choana and medication accumulated in the patient's nasal cavity adjacent the SPG.
Figure 7:
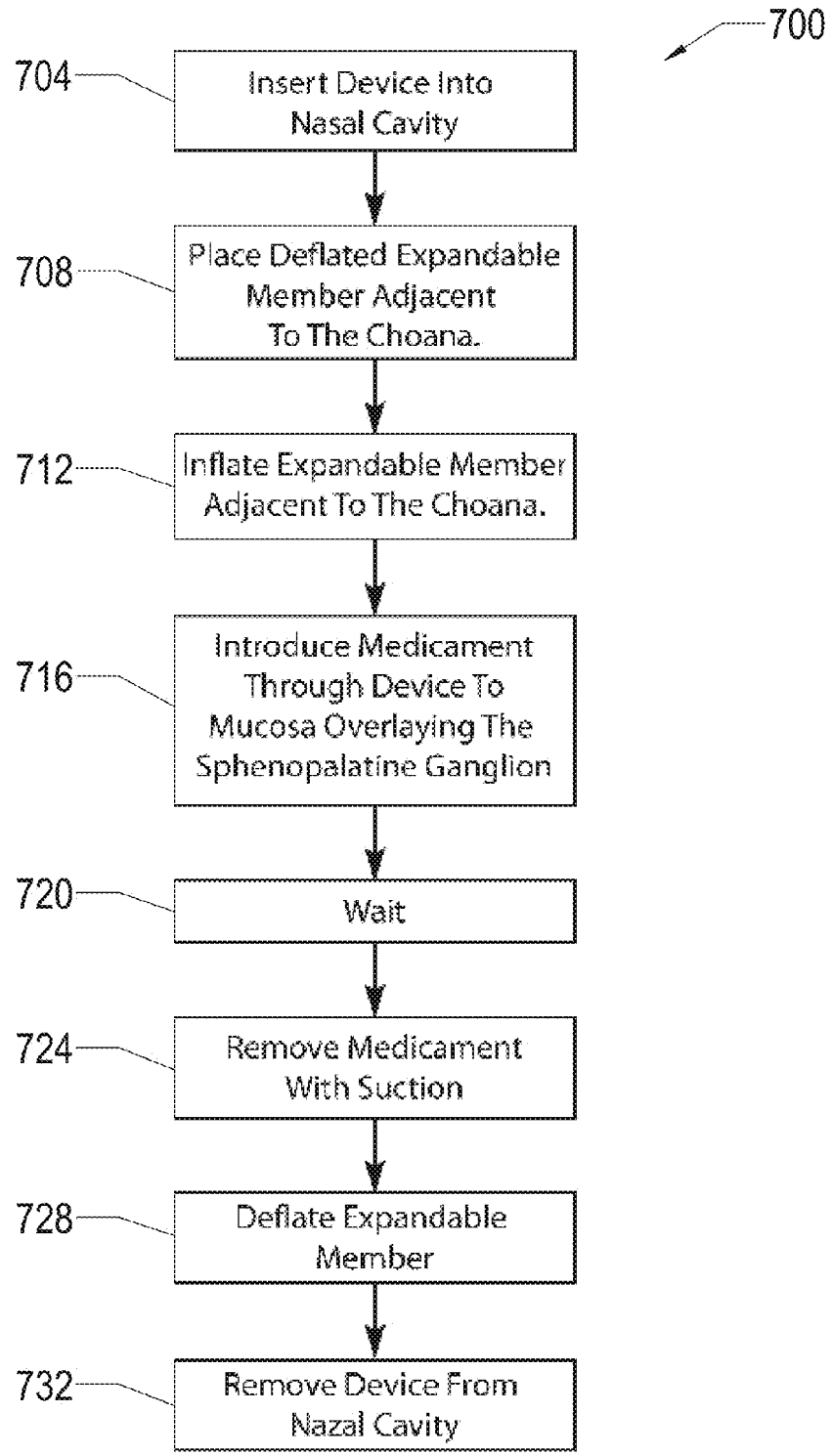
FIG. 7 is flow chart depicting a method of performing a surgical technique using a surgical device of the present disclosure.

Referring to FIG. 7, there is depicted a flow chart 700 representing at least some of the steps for performing a sphenopalatine ganglion block procedure utilizing the surgical device 100 of the present disclosure. Some of the steps of the flow chart 700 are illustrated in FIGS. 6A-6E. Step 704, which is illustrated in FIG. 6A, includes inserting the surgical device 100 into the patient's nasal cavity through one of the patient's nostrils (i.e., left nostril or right nostril). Specifically, the distal portion of the distal end 124 of the elongated flexible tubular member 108 is preferably inserted into the patient's nostril, while the expandable member 116 is entirely or partially deflated, and directed into the channel below the inferior turbinate and above the hard palate. It may also be preferable at the time of insertion of the surgical device 100 or shortly thereafter, that the illumination device 216 be activated. Upon activating the illumination device 216, light will transmit through the patient's hard palate. For example, when the distal end 124 of the elongated flexible tubular member 108 (and the illumination device 216) is located within the patient's nasal cavity as depicted in FIG. 6A, the illumination device 216 will be located at or below the posterior inferior turbinate and above the hard palate and be visible to a clinician viewing the interior of the oral cavity (patient's mouth), particularly the bottom of the palate (roof of the patient's mouth), and the light will appear to be transilluminating therefrom within the patient's head.

Referring to FIG. 6B, while continuing to activate the illumination device 216 and while the expandable member 116 is entirely or partially deflated, the distal portion of the distal end 124 of the elongated flexible tubular member 108 is inserted further into the patient's nasal cavity. When the distal end 124 of the elongated flexible tubular member 108 (and the illumination device 216) is located within the patient's nasal cavity as depicted in FIG. 6B, the illumination device 216 will continue to be located below the anterior of the inferior turbinate above the anterior of the hard palate further towards the soft palate in comparison location depicted in FIG. 6A

Referring to FIG. 6C, while continuing to activate the illumination device 216 and while the expandable member 116 is entirely or partially deflated, the distal portion of the distal end 124 of the elongated flexible tubular member 108 is even inserted further into the patient's nasal cavity. When the distal end 124 of the elongated flexible tubular member 108 is located within the patient's nasal cavity as depicted in FIG. 6C, the illumination device 216 will be located above the soft palate, namely the nasopharynx, and the light will appear to be transilluminating therefrom. At this point, step 704 of FIG. 7 has been completed because the expandable member 116 is located at the desired position, namely in the nasopharynx adjacent the choana, Referring to FIG. 6D, when the illumination device 216 and the expandable member 116 are located in the nasopharynx adjacent the choana, the expandable member 116 is expanded by depressing plunger 164 of the syringe 112, as depicted in step 712 of FIG. 7, thereby blocking the choana. Once the choana is blocked, medication is introduced to the nasal cavity through the opening 160 of the flexible tubular member 108. As the medication is introduced, the expanded expandable member 116 prevents the flow of medication down the patient's throat. And because the patient's head it typically tilted backwards during this procedure, the medication collects proximally above the expandable member 116. Accordingly, the medication begins to accumulate within the nasal cavity. Upon a certain volume, such as 5 milliliters to 10 milliliters of medication being introduced to the nasal cavity through the opening 160, the level of medication rises within the nasal cavity, namely the sphenopalatine fossa, such that the medication contacts the mucosa overlaying the SPG. Introducing the medication in this fashion and maintaining the desired level of medication provides for direct and sustained contact with the mucosa overlaying the SPG. The medication is absorbed by the permeable mucosa overlaying the SPG. In comparison to spraying the mucosa with the medication, the device(s) and method(s) of the present disclosure provide direct and sustained contact with the mucosa and SPG, which is a more effective treatment. Also, varying the medication and contact times may further increase the effectiveness of the treatment. Varying the medication and contact times also provide the clinician the flexibility to personalize the patient's treatment. Another example of the way in which the clinician may utilize the device(s) and method(s) of the present disclosure to personalize the patient's treatment includes inflating the inflatable member to a certain pressure.

As mentioned above, it may be preferable for the patient's head to be tilted backwards during the procedure. Referring to FIG. 6E, it may be preferable for the patient's head to be tilted at an angle (a) between 0 degrees and 90 degrees, and more preferable for the patient's head to be tilted at an angle (a) between 15 degrees and 75 degrees, and further preferable for the patient's head to be tilted at an angle (a) between 30 degrees and 60 degrees, and even further preferable for the patient's head to be tilted at an angle (a) of about 45 degrees. Tilting the patient's head during the procedure allows the medication 602 to collect above the inflatable member 116 and contact the mucosa overlaying the SPG.

It may also be desirable to prevent the medication from being introduced or sprayed into the nasal cavity in an unknown direction. That is, it may be desirable to control the introduction of the medication into the nasal cavity such that the medication collects within the nasal cavity above the expandable member, forms a pool of medication 602, and the level of medication raises to sphenopalatine fossa and/or the mucosa overlaying the SPG without randomly spraying the medication into the nasal cavity. Controlling the introduction of the medication in this manner increases the likelihood that that medication reaches the mucosa overlaying the SPG and the SPG itself. Referring to FIG. 9, there is a means for controlling the direction from which the medication exits the flexible tubular member 108 and is introduced to the nasal cavity. Such means may include a deflector 902 that directs the flow of medication exiting the flexible tubular member 108 toward the expandable member 116. Directing the flow of medication toward the expandable member 116 reduces the likelihood that the medication will be distributed, via spraying, in an unknown direction. As illustrated in FIG. 9, the deflector 902 is coupled to the flexible tubular member 108. The deflector 902 can be located exteriorly of the flexible tubular member 108, such as in the form of a sleeve that surrounds the opening 160, thereby forcing the outflow of medication towards the inflatable member 116. The deflector 902 can also be integral with the flexible tubular member 108, such that the portion of the flexible tubular member 108 adjacent the opening 160 directs the outflow of medication towards the inflatable member 116. The deflector 902 may also be a separate component that is inserted at least partially within the flexible tubular member 108 and directs the outflow of medication towards the inflatable member 116.

Referring to step 720 of FIG. 7, it may be preferable for the medication to remain within the nasal cavity and contact the mucosa overlaying the SPG, as well as the SPG, for a predetermined period of time (e.g., about 20 minutes), as discussed above. Referring to step 730, upon the SPG being directly exposed to the medication for the desired period, the medication is removed from the nasal cavity by suctioning the medication through the opening 160 with an auxiliary syringe. Once the medication is removed, the expandable member 116 may be collapsed by retracting the plunger 164 of the syringe 112, as depicted in step 728 of FIG. 7. As set forth in step 732, after the medication is removed and the expandable member 116 is collapsed, the surgical device 100 may be removed from the nasal cavity.

The procedure discussed above with respect to FIG. 7 performs a sphenopalatine ganglion block for one SPG located on one (i.e., left or right) side of the patient's head. Upon completing the sphenopalatine ganglion block for one side of the head, the same procedure can be repeated by inserting the distal end of the elongated flexible tubular member 108 into the patient's other nostril and applying the medication to the other SPG.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for delivering a medication to a sphenopalatine ganglion of a patient, the method comprising the steps of:
   (a) inserting a device into a portion of a nasal cavity of a patient through a nostril, the device comprising:
      a handle comprising a proximal end and a distal end;
      an inflation device at least partially and integrally disposed within the handle;
      a flexible tubular member extending from the distal end of the handle, the flexible tubular member comprising a proximal end, a distal end, an inflation lumen coupled to the plunger and extending from the proximal end of the flexible tubular member, and a second lumen extending from the proximal end of the flexible tubular member to a port;
      an expandable member attached to the flexible tubular member, the expandable member comprising a proximal end and as distal end, wherein the inflation lumen opens into the expandable member, wherein the port is disposed proximally of the proximal end of the expandable member; and
      an illumination device disposed adjacent the distal end of the flexible tubular member and distally of the expandable member; and
   (b) activating the illumination device;
   (c) placing the expandable member adjacent the patient's choana;
   (d) expanding the expandable member adjacent the patient's choana;
   (e) introducing a medication to sphenopalatine ganglion through the port in the flexible tubular member;
   (f) removing at least a portion of the medication through the port in the flexible tubular member;
   (g) collapsing the expandable member; and
   (h) removing the device from the nasal cavity.

2. The method of claim 1 further comprising inserting the device into a second portion of the nasal cavity of the patient through a second nostril and performing steps (a) through (h).

3. The method of claim 1 further comprising the step of allowing the medication to collect above the expandable member.

4. The method of claim 3 further comprising the step of allowing the medication to collect above the expandable member for a period of 5 minutes to 20 minutes.

5. The method of claim 3 further comprising the step of allowing the medication to collect above the expandable member for a period of 5 minutes to 35 minutes.

6. The method of claim 5 wherein the medication collects above the expandable member for a period of 10 minutes to 30 minutes.

7. The method of claim 6 wherein the medication collects above the expandable member for a period of 15 minutes to 25 minutes.

8. The method of claim 7 wherein the medication collects above the expandable member for a period of 20 minutes.

9. The method of claim 3 wherein the volume of introducing through the port in the flexible tubular member is between 2 milliliters and 15 milliliters.

10. The method of claim 9 wherein the volume of introducing through the port in the flexible tubular member is between 5 milliliters and 10 milliliters.

11. The device of claim 1, wherein the plunger comprises a housing, wherein the housing comprises a distal end and an opening disposed proximally of the housing's distal end.

12. The device of claim 1, wherein the handle further comprises a switch for activating the illumination device.

13. The device of claim 12, wherein the handle further comprises a power supply for the illumination device.

14. The device of claim 13, wherein the flexible tubular member comprises a conductor that couples the power supply to the illumination device.

* * * * *